United States Patent
Paul et al.

(10) Patent No.: US 8,519,273 B2
(45) Date of Patent: *Aug. 27, 2013

(54) CIRCUIT MATERIALS WITH IMPROVED BOND, METHOD OF MANUFACTURE THEREOF, AND ARTICLES FORMED THEREFROM

(76) Inventors: Sankar Paul, Branford, CT (US); Dirk M. Baars, South Windsor, CT (US)

( * ) Notice: Subject to any disclaimer, the term of this patent is extended or adjusted under 35 U.S.C. 154(b) by 130 days.

This patent is subject to a terminal disclaimer.

(21) Appl. No.: 12/937,018

(22) PCT Filed: Feb. 13, 2009

(86) PCT No.: PCT/US2009/034058
§ 371 (c)(1),
(2), (4) Date: Oct. 8, 2010

(87) PCT Pub. No.: WO2009/126366
PCT Pub. Date: Oct. 15, 2009

(65) Prior Publication Data
US 2011/0031003 A1   Feb. 10, 2011

Related U.S. Application Data

(60) Provisional application No. 61/043,785, filed on Apr. 10, 2008.

(51) Int. Cl.
*H05K 1/00* (2006.01)
(52) U.S. Cl.
USPC ............ 174/258; 174/256; 174/259; 174/255
(58) Field of Classification Search
USPC ................................. 174/250–260
See application file for complete search history.

(56) References Cited

U.S. PATENT DOCUMENTS 2,739,881 A * 3/1956 Kepple .......................... 174/259
4,306,933 A * 12/1981 Da Fonte, Jr. ................. 216/109

(Continued)

FOREIGN PATENT DOCUMENTS

EP   0707038 A1   9/1995
GB   2172892 A1   10/1986

(Continued)

OTHER PUBLICATIONS

DE 19650370 A1, Publication Date: Jun. 10, 1998, Abstract, 1 page.

(Continued)

*Primary Examiner* — Hoa C Nguyen
*Assistant Examiner* — Paresh Paghadal
(74) *Attorney, Agent, or Firm* — Cantor Colburn LLP

(57) ABSTRACT

A circuit subassembly, comprising: a conductive layer, a dielectric layer formed from a thermosetting composition, wherein the thermosetting composition comprises, based on the total weight of the thermosetting composition a polybutadiene or polyisoprene resin, about 30 to about 70 percent by weight of a magnesium hydroxide having less than about 1000 ppm of ionic contaminants, and about 5 to about 15 percent by weight of a nitrogen-containing compound, wherein the nitrogen-containing compound comprises at least about 15 weight percent of nitrogen; and an adhesive layer disposed between and in intimate contact with the conductive layer and the dielectric layer, wherein the adhesive comprises a poly(arylene ether), wherein the circuit subassembly has a UL-94 rating of at least V-1.

22 Claims, 2 Drawing Sheets

(56) References Cited

U.S. PATENT DOCUMENTS

| | | | |
|---|---|---|---|
| 4,874,826 | A | 10/1989 | Sakamoto et al. |
| 4,954,185 | A | 9/1990 | Kohm |
| 5,124,415 | A | 6/1992 | Sakamotot et al. |
| 5,194,307 | A | 3/1993 | Gardeski |
| 5,223,568 | A | 6/1993 | Landi et al. |
| 5,310,820 | A | 5/1994 | Nelissen et al. |
| 5,541,243 | A | 7/1996 | Ohmura et al. |
| 5,569,545 | A | 10/1996 | Yokono et al. |
| 5,571,609 | A | 11/1996 | St. Lawrence et al. |
| 5,622,782 | A | 4/1997 | Poutasse et al. |
| 6,132,851 | A | 10/2000 | Poutasse |
| 6,165,309 | A | 12/2000 | Burnell et al. |
| 6,218,454 | B1 * | 4/2001 | Nosu et al. ............ 524/433 |
| 6,352,782 | B2 | 3/2002 | Yeager et al. |
| 6,528,559 | B1 | 3/2003 | Nakacho et al. |
| 7,022,404 | B2 * | 4/2006 | Sethumadhavan et al. ............ 428/295.1 |
| 7,090,924 | B2 | 8/2006 | Sharma et al. |
| 7,582,691 | B2 * | 9/2009 | Peters et al. ............ 524/100 |
| 8,257,820 | B2 * | 9/2012 | Paul et al. ............ 428/195.1 |
| 2003/0183598 | A1 * | 10/2003 | Kologe et al. ............ 216/13 |
| 2005/0107497 | A1 | 5/2005 | Akaho |
| 2005/0112369 | A1 | 5/2005 | Ibbitson et al. |
| 2005/0159516 | A1 | 7/2005 | Kwon |
| 2005/0208278 | A1 | 9/2005 | Landi et al. |
| 2008/0038528 | A1 * | 2/2008 | Paul ............ 428/219 |
| 2009/0151984 | A1 | 6/2009 | Fujimura |

FOREIGN PATENT DOCUMENTS

| | | | |
|---|---|---|---|
| JP | 1026555 | A | 1/1989 |
| JP | 4258658 | A | 9/1992 |
| JP | 1997031220 | A | 2/1997 |
| JP | 1999012456 | A | 1/1999 |
| JP | 1999209568 | A | 1/1999 |
| JP | 2005105061 | A | 4/2005 |
| JP | 2007126605 | A | 5/2007 |
| JP | 2007302877 | A | 11/2007 |
| WO | 9957949 | A1 | 11/1999 |
| WO | 02/083328 | A1 | 10/2002 |
| WO | 03048249 | A1 | 6/2003 |
| WO | 2008/020984 | A2 | 2/2008 |
| WO | 2008/127970 | A2 | 10/2008 |
| WO | 2009/126366 | A2 | 10/2009 |
| WO | 2010/009381 | A1 | 1/2010 |

OTHER PUBLICATIONS

International Searching Authority, International Search Report, PCT/US2007/016987, Mailing date: Feb. 21, 2008, 6 pages.
International Searching Authority, International Search Report, PCT/US2009/034058, Date of mailing: Sep. 24, 2009, 7 pages.
International Searching Authority, Written Opinion, PCT/US2007/016987, Date of mailing: Feb. 21, 2008, 6 pages.
International Searching Authority, Written Opnion, PCT/US2009/034058, Date of mailing: Sep. 24, 2009, 7 pages.
The International Searching Authority, Communication in Cases for Which No Other Form Is Applicable, PCT/US2010/038303, Date of Mailing: Feb. 16, 2011, 1 page.
JP2005105062 A; Publication date: Apr. 21, 2005, Abstract, 1 page.
The International Searching Authority, International Search Report, PCT/US2010/038303, Date of Mailing Feb. 15, 2011, 7 pages.
The International Searching Authority, Written Opinion, PCT/US2010/038303, Date of Mailing Feb. 15, 2011, 10 pages.
The International Bureau, Preliminary Report on Patentability, PCT/US2009/034058, International Filing Date: Feb. 13, 2009, 8 pages.
The International Searching Authority, International Search Report, PCT/US2010/038303, Date of mailing: Nov. 23, 2010, 9 pages.
The International Searching Authority, Written Opinion, PCT/US2010/038303, Date of mailing: Nov. 23, 2010, 10 pages.
JP08-208778 Abstract, Date of publication: Aug. 13, 1996, Abstract, 1 page.
JP09-001728, Date of publication: Jan. 7, 1997, Abstract, 1 page.
JP2001-127444, Date of publication: May 11, 2001, Abstract, 1 page.
JP2001-329147, Date of publication: Nov. 27, 2001, Abstract, 1 page.
JP2001-339131, Date of publication: Dec. 7, 2001, Abstract, 1 page.
JP2004-091533, Date of publication: Mar. 25, 2004, Abstract, 1 page.
JP2005-060489, Date of publication: Mar. 10, 2005, Abstract, 1 page.
JP2005-336426, Date of publication: Dec. 8, 2005, Abstract, 1 page.
JP2006-051687, Date of publication: Feb. 23, 2006, Asbtract, 1 page.
JP2006-205694, Date of publication: Aug. 10, 2006, Abstract, 1 page.
JP2007-021763, Date of publication: Feb. 1, 2007, Abstract, 1 page.
JP08-208778 Date of publication: Aug. 13, 1996, Abstract, 1 page.

* cited by examiner

CIRCUIT MATERIALS WITH IMPROVED BOND, METHOD OF MANUFACTURE THEREOF, AND ARTICLES FORMED THEREFROM

BACKGROUND

This invention generally relates to circuit subassemblies, methods of manufacture of the circuit subassemblies, and articles formed therefrom, including circuits and multi-layer circuits.

As used herein, a circuit subassembly is an article used in the manufacture of circuits and multi-layer circuits, and includes circuit laminates, packaging substrate laminates, and build-up materials, bond plies, resin coated conductive layers, and cover films. A circuit laminate is a type of circuit subassembly that has a conductive layer, e.g., copper, fixedly attached to a dielectric substrate layer. Double clad laminates have two conductive layers, one on each side of the dielectric layer. Patterning a conductive layer of a laminate, for example by etching, provides a circuit. Multilayer circuits comprise a plurality of conductive layers, at least one of which contains a conductive wiring pattern. Typically, multilayer circuits are formed by laminating one or more circuit layers together using bond plies and, in some cases, resin coated conductive layers, in proper alignment using heat and/or pressure. After lamination to form the multilayer circuit, known hole-forming and plating technologies can be used to produce useful electrical pathways between conductive layers.

Historically, circuit subassembly dielectrics have been made with glass fabric-reinforced epoxy resins. The relatively polar epoxy material bonds comparatively well to metallic surfaces such as copper foil. However, the polar groups in the epoxy resin also lead to a relatively high dielectric constant and high dissipation factor. Electronic devices that operate at higher frequencies require use of circuit dielectric material with low dielectric constants and low dissipation factors. Better electrical performance is achieved by using comparatively nonpolar resin systems, such as those based on polybutadiene, polyisoprene, or polyphenylene oxide polymer systems. An unwanted consequence of the lower polarity of these resins systems is an inherently lower bond to metallic surfaces.

In addition, as electronic devices and the features thereon become smaller, manufacture of dense circuit layouts is facilitated by use of circuit dielectric materials with a high glass transition temperature. However, when dielectric substrates with low dielectric constants, low dissipation factors, and high glass transition temperatures are used, adhesion between the conductive layer and the dielectric substrate layer can be reduced. Adhesion can be even more severely reduced when the conductive layer is a low or very low roughness copper foil (low profile copper foil). Such foils are desirably used in dense circuit designs to improve the etch definition and in high frequency applications to lower the conductor loss due to roughness.

A number of efforts have been made to improve the bonding between dielectric circuit substrates and the conductive layer surface. For example, use of various specific polymeric compositions has been disclosed. PCT Application No. 99/57949 to Holman discloses using an epoxy or phenoxy resin having a molecular weight greater than about 4,500 to improve the peel strength of a circuit laminate. U.S. Pat. No. 6,132,851 to Poutasse also discloses use of a phenolic resole resin/epoxy resin composition-coated metal foil as a means to improve adhesion to circuit substrates. U.S. Pat. No. 4,954,185 to Kohm describes a two-step process for producing a coated metal foil for printed circuit board laminates, the first being a chemical process to create a metal oxide layer on the metal substrate surface, and the second being the application of a poly(vinyl acetal)/thermosetting phenolic composition. Gardeski, in U.S. Pat. No. 5,194,307, describes an adhesive composition having one or more epoxy components and a high molecular weight polyester component. The cured adhesive layer is flexible and can be used for bonding metal foil to flexible circuit substrate (e.g., polyimide film). Yokono et al. describe improved adhesion in a copper clad circuit laminate in U.S. Pat. No. 5,569,545, obtained by use of various sulfur-containing compounds that presumably crosslink with the resin and chemically bond to the copper. The presence of sulfur-containing compounds can be undesirable, giving rise to an increased tendency to corrode. U.S. Patent Publication No. 2005/0208278 to Landi et al. discloses the use of an adhesion-promoting elastomeric layer comprising a non-sulfur curing agent. However, in practice it has been found that the elastomeric adhesion promoting layers can result in a soft surface, increasing the possibility of handling damage during processing. Finally, Poutasse and Kovacs, in U.S. Pat. No. 5,622,782, use a multi-component organosilane layer to improve foil adhesion with another substrate. Copper foil manufacturers can apply a silane treatment to their foils as the final production step, and the silane composition, which is often proprietary, is commonly selected to be compatible with the substrate of the customer.

As noted by Poutasse et al. in U.S. Pat. No. 5,629,098, adhesives that provide good adhesion to metal and substrate (as measured by peel strength) generally have less than satisfactory high temperature stability (as measured in a solder blister resistance test). Conversely, adhesives that provide good high temperature stability generally have less than satisfactory adhesion. There accordingly remains a need in the art for methods for improving the bond between a conductive metal and a circuit substrate, particularly thin, rigid, thermosetting substrates having low dielectric constants, low dissipation factors, and high glass transition temperatures, that maintains adhesiveness at high temperatures. It would be advantageous if the adhesive did not require B-staging, and/or that use of the adhesive did not adversely affect the electrical and mechanical properties of the resulting circuit materials.

Further, because circuit subassembly materials can contain synthetic organic materials with carbon and often high hydrogen contents, they can be combustible, and many applications demand that they meet flame retardancy requirements mandated by various manufacturing sectors such as the building, electrical, transportation, mining and automotive industries. To meet these stipulations, additives are used that interfere in various ways with the chemical exothermic chain of combustion Electrical circuit subassembly compositions have typically used halogenated, particularly brominated, flame retardant additives to achieve the necessary levels of flame retardancy. In recent years, brominated flame retardants have come under scrutiny for their potential to contribute to health and environmental problems; therefore, it has become desirable to have circuit subassemblies which include flame retardant additives that are effective, yet that do not contain halogens, especially bromine and chlorine.

Alternative commonly used flame retardant additives for polymers that do not contain halogen have serious drawbacks if used in circuit subassemblies, either because of their inherent properties, or because they are less effective as flame retardants. The former drawback can lead to poor electrical properties, decreased thermal stability, and increased water absorption. The latter drawback might be overcome by use of very high loadings, but this can lead to porosity and deterioration of physical properties. These noted problems of common alternate flame retardants are exacerbated when used with a highly flammable resin system. Examples of alternative flame retardants giving these problems are flame retardant phosphorous compounds, aluminum trihydrate, borates, and the like.

Accordingly, there remains a need for non-halogen containing flame retardant thermosetting compositions that provide the desired flame retardant properties without impairing physical properties such as electrical and moisture absorption properties. It would be equally desirable to provide a rigid halogen-free circuit subassembly having good flame retardant properties as well as having improved bonding with conductive metal materials.

SUMMARY OF INVENTION

In one embodiment, a circuit subassembly includes a conductive layer, a dielectric layer formed from a thermosetting composition wherein the thermosetting composition comprises, based on the total weight of the thermosetting composition: a polybutadiene or polyisoprene resin, about 30 to about 70 percent by weight of a magnesium hydroxide having less than about 1000 ppm of ionic contaminants, and about 5 to about 15 percent by weight of a nitrogen-containing compound, wherein the compound comprises at least about 15 weight percent of nitrogen; and an adhesive layer disposed between and in intimate contact with the conductive layer and the dielectric layer, wherein the adhesive comprises a poly(arylene ether), wherein the circuit subassembly has a UL-94 rating of at least V-1. In one embodiment, the adhesive further comprises a polybutadiene or polyisoprene polymer, preferably a carboxy-functionalized polybutadiene or polyisoprene polymer, and optionally an elastomer.

In another embodiment, a circuit subassembly comprises: a conductive layer; and a dielectric layer formed from a thermosetting composition, wherein the thermosetting composition comprises, based on the total weight of the thermosetting composition: a polybutadiene or polyisoprene resin, about 30 to about 70 percent by weight, of a magnesium hydroxide having less than about 1000 ppm of an ionic contaminant, and about 5 to about 15 percent by weight of a nitrogen-containing compound, wherein the nitrogen-containing compound comprises at least about 15 weight percent of nitrogen; and wherein the circuit subassembly has a UL-94 rating of at least V-1.

In yet another embodiment, a circuit subassembly comprises: a conductive layer; a dielectric layer formed from a thermosetting composition, wherein the thermosetting composition comprises, based on the total weight of the thermosetting composition a polybutadiene or polyisoprene resin, and about 50 to about 80 percent by weight, of a magnesium hydroxide having less than about 1000 ppm of an ionic contaminant; and an adhesive layer disposed between and in intimate contact with the conductive layer and the dielectric layer, wherein the adhesive layer comprises a poly(arylene ether); wherein the circuit material has a UL-94 rating of at least V-1. In one embodiment, the adhesive further comprises a polybutadiene or polyisoprene polymer, preferably a carboxy-functionalized polybutadiene or polyisoprene polymer, and optionally an elastomer.

In another alternative embodiment, a circuit subassembly comprises: a conductive layer; and a dielectric layer formed from a thermosetting composition, wherein the thermosetting composition comprises, based on the total weight of the thermosetting composition: a polybutadiene or polyisoprene resin, and about 50 to about 80 percent by weight, of a magnesium hydroxide having less than about 1000 ppm of an ionic contaminant; wherein the circuit material has a UL-94 rating of at least V-1.

Still another embodiment is a circuit subassembly, comprising: a dielectric layer formed from a thermosetting composition, wherein the thermosetting composition comprises, based on the total weight of the thermosetting composition: a polybutadiene or polyisoprene resin; about 30 to about 70 percent by weight of a magnesium hydroxide having less than about 1000 ppm of ionic contaminants; and about 5 to about 15 percent by weight of a nitrogen-containing compound, wherein the compound comprises at least about 15 weight percent of nitrogen; wherein the circuit subassembly has a UL-94 rating of at least V-1.

The invention is further illustrated by the following drawings, detailed description, and examples.

BRIEF DESCRIPTION OF DRAWINGS

Referring now to the exemplary drawings wherein like elements are numbered alike in the several figures.

DETAILED DESCRIPTION

Figure 1:
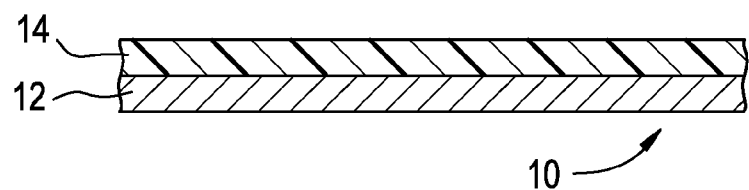
FIG. 1 shows an exemplary circuit subassembly with an adhesive layer disposed on a conductive layer, e.g., a copper foil.

The circuit subassemblies disclosed herein are based on polymer systems which, while having the outstanding electrical properties desired in many modern applications, can be highly flammable, and can have poor adhesion to conductive metals. In the past, the problem of high flammability has been addressed by addition to the polymer system of brominated organic flame retardants. These brominated compounds are similar to the type used in other circuit materials to increase flame resistance. In recent years, however, there has been increasing, worldwide health and environmental concerns regarding these brominated compounds because of their alleged potential to yield toxic, even carcinogenic, by-products when burned or when disposed in landfills.

These concerns have spurred desires for 'halogen-free' circuit materials that have a UL94 flame retardance rating of V-1 or better without the use of halogens, especially bromine and chlorine. Some government and other groups have proposed that the specification for 'halogen-free' in a circuit material be less than 900 parts per million (ppm) of bromine, chlorine, or a combination thereof.

The circuit subassemblies disclosed herein advantageously comprise non-polar polymer systems with halogen-free additives, which achieve flame retardance of V-1 or better while also giving good electrical properties, low water absorption, good adhesion to conductive metals, and excellent resistance to the solvents and solutions, especially the highly acidic ones, used in conventional circuit fabrication. These properties are all highly desired in circuit subassemblies for use in high frequency or high circuit density applications.

U.S. Pat. No. 7,022,404 B2 discloses use of a combination of flame retardants, specifically, magnesium hydroxide and polytetrafluoroethylene (PTFE), to achieve a UL94 rating of V-1 or better with the flammable resin systems of this invention, and without the use of added bromine or chlorine. This combination, however, can have deficiencies caused, at least in part, by the high loading of the additives required for the desired flame retardance, in particular, higher-than-desired water absorption, and poorer-than-desired acid resistance and adhesion to conductive metals.

The present disclosure addresses these deficiencies while achieving a UL94 rating of V-1 or better. This is accomplished by reducing the amount of magnesium hydroxide by adding a nitrogen-containing compound, or combination of such compounds, which has a nitrogen content of at least about 15 percent by weight (wt %), along with use of a bond improvement adhesive composition between the circuit dielectric and a conductive metal. The resulting circuit subassemblies have the unexpected, but desirable combination of properties of a V-1 rating or better, low water absorption, good electrical characteristics, strong resistance to acids, and excellent adhesion to conductive metals, all while being halogen-free.

Accordingly, described herein are circuit subassemblies comprising halogen-free dielectric material compositions that can incorporate bond improvement adhesive layer compositions.

The bond improvement adhesive compositions comprise a poly(arylene ether); optionally, a polybutadiene or polyisoprene polymer, preferably including a carboxylated polybutadiene or polyisoprene polymer; and optionally, an elastomeric block copolymer comprising units derived from an alkenyl aromatic compound and a conjugated diene. The poly(arylene ether) can also optionally be carboxy-functionalized. The combination of these components provides enhanced adhesion between a conductive metal layer and a circuit substrate, as well as improved flame resistance. The improved bond strength is advantageously maintained at high temperatures, such as those encountered during soldering operations (e.g., 550° F. or 288° C.). In a particularly advantageous feature, use of the adhesive composition does not significantly adversely affect the electrical properties of the resultant circuit laminate, such as low dielectric constant, low dissipation factor, low water absorption, and improved dielectric breakdown strength.

The poly(arylene ether) can be in the form of a homopolymer or a copolymer, including a graft or a block copolymer. Combinations of various forms can be used. Poly(arylene ether)s comprise a plurality of structural units of formula (1):

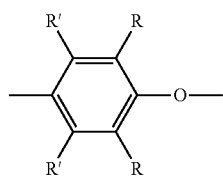

(1)

wherein for each structural unit, each R and R' is independently hydrogen, primary or secondary $C_{1-7}$ alkyl, phenyl, $C_{1-7}$ aminoalkyl, $C_{1-7}$ alkenylalkyl, $C_{1-7}$ alkynylalkyl, $C_{1-7}$ alkoxy, $C_{6-10}$ aryl, and $C_{6-10}$ aryloxy. In some embodiments, each R is independently $C_{1-7}$ alkyl or phenyl, for example, $C_{1-4}$ alkyl, and each R' is independently hydrogen or methyl.

Exemplary poly(arylene ether)s include poly(2,6-dimethyl-1,4-phenylene ether), poly(2,6-diethyl-1,4-phenylene ether), poly(2,6-dipropyl-1,4-phenylene ether), poly(2-methyl-6-alkyl-1,4-phenylene ether), poly(di-tert-butyl-dimethoxy-1,4-phenylene ether), poly(2,6-dichloromethyl-1,4-phenylene ether, poly(2,6-dibromomethyl-1,4-phenylene ether), poly(2,6-di(2-chloroethyl)-1,4-phenylene ether), poly(2,6-ditolyl-1,4-phenylene ether), poly(2,6-dichloro-1,4-phenylene ether), poly(2,6-diphenyl-1,4-phenylene ether), and poly(2,5-dimethyl-1,4-phenylene ether). A useful poly(arylene ether) comprises 2,6-dimethyl-1,4-phenylene ether units, optionally in combination with 2,3,6-trimethyl-1,4-phenylene ether units.

The poly(arylene ether) can be functionalized so as to provide a functional group that enhances adhesion between a conductive metal layer and a circuit substrate layer. Functionalization can be accomplished using a polyfunctional compound having in the molecule both (i) a carbon-carbon double bond or a carbon-carbon triple bond, and (ii) one or more of a carboxy group, including a carboxylic acid, anhydride, amide, ester, or acid halide. In one embodiment the functional group is a carboxylic acid or ester group. Examples of polyfunctional compounds that can provide a carboxylic acid functional group include maleic acid, maleic anhydride, fumaric acid, and citric acid.

In particular, suitable functionalized poly(arylene ether)s include the reaction product of a poly(arylene ether) and a cyclic carboxylic acid anhydride. Examples of suitable cyclic anhydrides are maleic anhydride, succinic anhydride, glutaric anhydride, adipic anhydride, and phthalic anhydride, more specifically, maleic anhydride. Modified poly(arylene ethers) such as maleinated poly(arylene ethers) can be produced by methods as described in U.S. Pat. No. 5,310,820, or are commercially available. Examples of commercially available suitable modified and unmodified poly(arylene ethers) include PPE-MA from Asahi (a maleinized poly(arylene ether)), and Blendex HPP820 from Chemtura (an unmodified poly(arylene ether)).

In some embodiments, the adhesives further comprise a polybutadiene or polyisoprene polymer. In a specific embodiment, combination comprising two or more polybutadiene and/or polyisoprene polymers are used. A "polybutadiene or polyisoprene polymer" as used herein includes homopolymers derived from butadiene, homopolymers derived from isoprene, and copolymers derived from butadiene and/or isoprene and/or less than 50 wt % of a monomer co-curable with the butadiene and/or isoprene. In other words, the copolymer of butadiene and/or isoprene comprise polymers with greater than 50 wt. % butadiene, greater than 50% isoprene, or greater than 50% of butadiene plus isoprene. Suitable monomers co-curable with butadiene and/or isoprene include monoethylenically unsaturated compounds such as acrylonitrile, ethacrylonitrile, methacrylonitrile, alpha-chloroacrylonitrile, beta-chloroacrylonitrile, alpha-bromoacrylonitrile, $C_{1-6}$ alkyl (meth)acrylates (for example, methyl (meth)acrylate, ethyl (meth)acrylate, n-butyl (meth)acrylate, n-propyl (meth)acrylate, and isopropyl (meth)acrylate), acrylamide, methacrylamide, maleimide, N-methyl maleimide, N-ethyl maleimide, itaconic acid, (meth)acrylic acid, styrene, alkenyl aromatic compounds as described below, and a combination comprising at least one of the foregoing monoethylenically unsaturated monomers.

In another advantageous embodiment, the polybutadiene polymer comprises a syndiotactic polybutadiene homopolymer with no co-curable monomer. The syndiotactic polybutadiene homopolymer is often used in combination with a different polybutadiene polymer, a polyisoprene polymer, or a combination thereof.

The polybutadiene or polyisoprene polymer(s) used in the adhesive composition can be co-curable with the poly (arylene ether). In one embodiment, the polybutadiene or polyisoprene polymer is carboxy-functionalized. Functionalization can be accomplished using a polyfunctional monomer co-curable with butadiene or isoprene, and which has in the molecule both (i) a carbon-carbon double bond or a carbon-carbon triple bond, and (ii) one or more of a carboxy group, including a carboxylic acid, anhydride, amide, ester, or acid halide. A preferred carboxy group is a carboxylic acid or ester. Examples of polyfunctional compounds that can provide a carboxylic acid functional group include maleic acid, maleic anhydride, fumaric acid, and citric acid. In particular, polybutadienes adducted with maleic anhydride can be used in the adhesive composition. Suitable maleinized polybutadiene polymers are commercially available, for example from Sartomer under the trade names RICON 130MA8, RICON 130MA13, RICON 130MA20, RICON 131MA5, RICON 131MA10, RICON 131MA17, RICON 131MA20, and RICON 156MA17. Suitable maleinized polybutadiene-styrene copolymers are commercially available, for example, from Sartomer under the trade names RICON 184MA6. RICON 184MA6 is a butadiene-styrene copolymer adducted with maleic anhydride having styrene content from 17 to 27 wt % and number average molecular weight (Mn) of about 9,900 g/mole. In a specific embodiment, a syndiotactic polybutadiene homopolymer is used in combination with a carboxy-functionalized polybutadiene, more specifically a maleinized polybutadiene homopolymer or copolymer, for example a maleinized polybutadiene-styrene.

In still other embodiments, the adhesives further comprise an elastomeric polymer. The elastomeric polymer can be co-curable with the poly(arylene ether) and/or the polybutadiene or isoprene resin. Suitable elastomers include elastomeric block copolymers comprising a block (A) derived from an alkenyl aromatic compound and a block (B) derived from a conjugated diene. The arrangement of blocks (A) and (B) includes linear and graft structures, including radial teleblock structures having branched chains. Examples of linear structures include diblock (A-B), triblock (A-B-A or B-A-B), tetrablock (A-B-A-B), and pentablock (A-B-A-B-A or B-A-B-A-B) structures as well as linear structures containing 6 or more blocks in total of A and B. Specific block copolymers include diblock, triblock, and tetrablock structures, and specifically the A-B diblock and A-B-A triblock structures.

The alkenyl aromatic compound providing the block (A) is represented by formula (2):

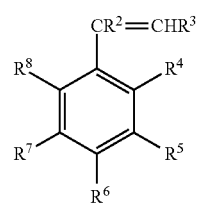

(2)

wherein each of $R^2$ and $R^3$ is independently hydrogen, $C_1$-$C_5$ alkyl, bromo, or chloro, and each of $R^4$, $R^5$, $R^6$, $R^7$, and $R^8$ is independently hydrogen, $C_1$-$C_{12}$ alkyl, $C_3$-$C_{12}$ cycloalkyl, $C_6$-$C_{12}$ aryl, $C_7$-$C_{12}$ aralkyl, $C_7$-$C_{12}$ alkaryl, $C_1$-$C_{12}$ alkoxy, $C_3$-$C_{12}$ cycloalkoxy, $C_6$-$C_{12}$ aryloxy, chloro, bromo, or hydroxy. Exemplary alkenyl aromatic compounds include styrene, 3-methylstyrene, 4-methylstyrene, 3,5-diethylstyrene, 4-n-propylstyrene, alpha-methylstyrene, alpha-methyl vinyltoluene, alpha-chlorostyrene, alpha-bromostyrene, dichlorostyrene, dibromostyrene, tetra-chlorostyrene, and the like, and combinations comprising at least one of the foregoing compounds. Styrene and/or alpha-methylstyrene are often used.

Specific examples of the conjugated dienes used to provide block (B) include 1,3-butadiene, 2-methyl-1,3-butadiene (isoprene), 2,3-dimethyl-1,3-butadiene, and 1,3-pentadiene, specifically 1,3-butadiene and isoprene. A combination of conjugated dienes can be used. The block (B) derived from a conjugated diene is optionally partially or fully hydrogenated.

Exemplary block copolymers comprising a block (A) derived from an alkenyl aromatic compound and block (B) derived from a conjugated diene include styrene-butadiene diblock copolymer (SB), styrene-butadiene-styrene triblock copolymer (SBS), styrene-isoprene diblock copolymer (SI), styrene-isoprene-styrene triblock copolymer (SIS), styrene-(ethylene-butylene)-styrene triblock copolymer (SEBS), styrene-(ethylene-propylene)-styrene triblock copolymer (SEPS), and styrene-(ethylene-butylene) diblock copolymer (SEB). Such polymers are commercially available, for example from Shell Chemical Corporation under the trade names KRATON D-1101, KRATON D-1102, KRATON D-1107, KRATON D-1111, KRATON D-1116, KRATON D-1117, KRATON D-1118, KRATON D-1119, KRATON D-1122, KRATON D-1135X, KRATON D-1184, KRATON D-1144X, KRATON D-1300X, KRATON D-4141, KRATON D-4158, KRATON G1726, and KRATON G-1652. KRATON D-1118 is a solid SB-SBS copolymer. This copolymer has polystyrene end blocks and a rubbery polybutadiene mid-block with about 20% SBS triblock and about 80% SB diblock. It is a low modulus, low cohesive strength, soft rubber.

The relative amount of the poly(arylene ether)s, the polybutadiene or polyisoprene polymer(s), and the elastomeric block copolymer will depend on the particular substrate material used, the desired properties of the circuit materials and circuit laminates, and like considerations. It has been found that use of a poly(arylene ether) provides increased bond strength between a conductive metal layer, particularly copper, and a relatively nonpolar dielectric substrate material. This result is particularly surprising since poly(arylene ether)s are themselves nonpolar. Use of a polybutadiene or polyisoprene polymer further increases high temperature resistance of the laminates, particularly when these polymers are carboxy-functionalized. Use of an elastomeric block copolymer can function to compatibilize the components of the adhesive. Determination of the appropriate quantities of each component can be done without undue experimentation, using the guidance provided herein.

In one embodiment, the adhesive composition comprises up to 100 wt % of the poly(arylene) ether, specifically the carboxy-functionalized poly(arylene ether). In another embodiment, the adhesive composition consists essentially of up to 100 wt % of the poly(arylene) ether, specifically the carboxy-functionalized poly(arylene) ether. In still another embodiment, the adhesive composition consists of up to 100 wt % of the poly(arylene) ether, specifically the carboxy-functionalized poly(arylene) ether.

The adhesive composition can alternatively comprise about 20 to about 99 wt %, specifically about 30 to about 80 wt %, more specifically about 40 to about 60 wt % of the poly(arylene ether), preferably the carboxy-functionalized poly(arylene ether), and about 1 to about 80 wt %, specifically about 20 to about 70 wt %, more specifically about 40 to about 60 wt % of the polybutadiene or polyisoprene polymer(s), preferably including the carboxy-functionalized polybutadiene or polyisoprene polymer, each of the foregoing amounts being based on the total weight of the polymer portion of the adhesive composition.

In still another embodiment, the adhesive composition comprises about 20 to about 98 wt %, specifically about 25 to about 75 wt %, more specifically about 30 to about 50 wt % of the poly(arylene ether), preferably the carboxy-functionalized poly(arylene ether); about 1 to about 79 wt %, specifically about 10 to about 60 wt %, more specifically about 20 to about 40 wt % of the co-curable polybutadiene or polyisoprene polymer(s), preferably including the co-curable carboxy-functionalized polybutadiene or polyisoprene polymer; and about 1 to about 79 wt %, specifically about 10 to about 60 wt %, more specifically about 20 to about 40 wt % of the elastomeric block copolymer, each based on the total weight of the polymer portion of the adhesive composition.

In addition to the one or more of the polymers described above, the adhesive composition can further optionally comprise additives such as curing agents, crosslinking agents, viscosity modifiers, coupling agents, wetting agents, flame retardants, fillers, and antioxidants. The particular choice of additives depends upon the nature of the conductive layer and the circuit substrate composition and are selected so as to enhance or not substantially adversely affect adhesion between a conductive layer and a circuit substrate, dielectric constant, dissipation factor, water absorbance, flame retardance, and/or other desired properties of the circuit material.

Suitable fillers for use in the adhesive composition include titanium dioxide (rutile and anatase), barium titanate, strontium titanate, silica, including fused amorphous silica, corundum, wollastonite, aramide fibers (e.g., KEVLAR™ from DuPont), fiberglass, $Ba_2Ti_9O_{20}$, glass spheres, quartz, boron nitride, aluminum nitride, silicon carbide, beryllia, alumina, magnesia, magnesium hydroxide, mica, talcs, nanoclays, aluminosilicates (natural and synthetic), and fumed silicon dioxide (e.g., Cab-O-Sil, available from Cabot Corporation), used alone or in combination. The fillers can be in the form of solid, porous, or hollow particles. Specific fillers include rutile titanium dioxide and amorphous silica. To improve adhesion between the fillers and polymer, the filler can be treated with one or more coupling agents, such as silanes, zirconates, or titanates. Fillers, when used, are typically present in an amount of about 15-60 volume %, specifically about 20-50 volume %, based on the total weight of the adhesive composition.

Suitable curing agents include those useful in initiating cure of the polymers, in the adhesive composition. Examples include, but are not limited to, azides, peroxides, sulfur, and sulfur derivatives. Free radical initiators are especially desirable as cure initiators. Examples of free radical initiators include peroxides, hydroperoxides, and non-peroxide initiators such as 2,3-dimethyl-2,3-diphenyl butane. Examples of peroxide curing agents include dicumyl peroxide, alpha, alpha-di (t-butylperoxy)-m,p-diisopropylbenzene, 2,5-dimethyl-2,5-di(t-butylperoxy)hexane-3, and 2,5-dimethyl-2,5-di(t-butylperoxy)hexyne-3, and mixtures comprising one or more of the foregoing cure initiators. The cure initiator, when used, is typically present in an amount of about 0.25 wt % to about 15 wt %, based on the total weight of the adhesive composition.

Crosslinking agents are reactive monomers or polymers that increase the cross-link density upon cure of the adhesive. In one embodiment, such reactive monomers or polymers are capable of co-reacting with a polymer in the adhesive polymer and a polymer in the circuit substrate composition. Examples of suitable reactive monomers include styrene, divinyl benzene, vinyl toluene, divinyl benzene, triallylcyanurate, diallylphthalate, and multifunctional acrylate monomers (such as Sartomer compounds available from Sartomer Co.), among others, all of which are commercially available. Useful amounts of crosslinking agents are about 0.1 to about 50 wt %, based on the total weight of the adhesive composition.

Suitable antioxidants include radical scavengers and metal deactivators. A non-limiting example of a free radical scavenger is poly[[6-(1,1,3,3-tetramethylbutyl) amino-s-triazine-2,4-dyil][(2,2,6,6,-tetramethyl-4-piperidyl)imino]hexamethylene[(2,2,6,6-tetramethyl-4-piperidyl)imino]], commercially available from Ciba Chemicals under the tradename Chimmasorb 944. A non-limiting example of a metal deactivator is 2,2-oxalyldiamido bis[ethyl 3-(3,5-di-t-butyl-4-hydroxyphenyl)propionate] commercially available from Uniroyal Chemical (Middlebury, Conn.) under the tradename Naugard XL-1. A single antioxidant or a mixture of two or more antioxidants can be used. Antioxidants are typically present in amounts of up to about 3 wt %, specifically about 0.5 to about 2.0 wt %, based on the total weight of the adhesive composition.

Coupling agents can be present to promote the formation of or participate in covalent bonds connecting a metal surface or filler surface with a polymer. Exemplary coupling agents include 3-mercaptopropylmethyldimethoxy silane and 3-mercaptopropyltrimethoxy silane. Coupling agents, when present, can be present in amounts of about 0.1 to about 1 wt %, based on the total weight of the adhesive composition.

The above-described adhesive composition can be used with a dielectric circuit substrate and a conductive layer to make circuit materials, circuit laminates, circuits, and multilayer circuits. Suitable conductive layers include a thin layer of a conductive metal such as a copper foil presently used in the formation of circuits, for example, electrodeposited copper foils. Useful copper foils typically have thicknesses of about 9 to about 180 micrometers.

The copper foil can be made either by the electrodeposition (ED) on a rotating stainless steel drum from a copper sulfate bath, or by the rolling of solid copper bars. Where ED copper foil is used, the initial roughness of the base foil is created in the foil plating process on the "bath side" (or matte side) of the foil. Additional roughness is created in a secondary plating step. Where rolled foil used, roughness is imparted to the initially smooth and shiny foil by a secondary plating step.

This mechanical roughness can result in several drawbacks. As described in detail by Brist et al. (Gary Brist, Stephen Hall, Sidney Clouser, and Tao Liang, "Non-classical conductor losses due to copper foil roughness and treatment," p. 26, *Circuitree*, can 2005) and Ogawa et al. (N. Ogawa, H. Onozeki, N. Moriike, T. Tanabe, T. Kumakura, "Profile-free foil for high-density packaging substrates and high-frequency applications," p. 457, Proceedings of the 2005 Electronic Components and Technology Conference, IEEE), the roughness on a conductor surface can result in a substantial increase in conductor loss at high frequencies, with a rough conductor causing up to twice the conductor loss of a smooth one. Ogawa also describes the limitations to accurate circuit fabrication, most notably the accurate etching of fine lines and spaces that are caused by conductor roughness.

The roughness of a copper foil is generally characterized by contact profilometry or optical interferometry. Most foil manufacturers measure roughness with a contact profilometer, due to their long history with such a measurement system. Most of the values cited herein were measured using a Veeco Instruments WYCO Optical Profiler, using the method of white light interferometry. Since the roughness can exist on several different scales and will consist of many peaks and valleys with varying distances from a fixed reference plane, there are many different ways to numerically characterize the surface roughness. Two frequently reported quantities are the RMS roughness value, Rq, and the peak-to-valley roughness, Rz, with both reported in dimensions of length.

Conventional ED copper foil made for the circuit industry has had treated side Rz values of 7 to 20 micrometers (um) (corresponding to Rq values of about 1.2 to 4 um) when measured by the WYCO Optical Profiler. Contact profilometers tend to yield lower values, due to the stylus deforming the copper treatment as the measurement is made. The treated side of rolled copper foil exhibits Rz values of 3.5-5.5 um (corresponding to Rq values of 0.45-0.9 um). "Reverse treated" ED foils, such as Oak-Mitsui MLS-TOC-500 can also exhibit Rq values similar to those of rolled foils. The lower profile ED foils currently exhibit Rz values of 2 to 3 um. By WYCO measurement, the shiny side of rolled foil exhibits an Rz value of about 0.7 um and a corresponding Rq of about 0.1 um.

More recently, other types of low profile electrodeposited foils have been commercially available. These include Oak Mitsui products SQ-VLP, with an Rq value measured by the WYCO of 0.7 um and MQ-VLP with a WYCO Rq value of 0.47 um.

Both rolled and ED foils specially treated for the circuit industry are available from a number of commercial manufacturers. For example, low profile copper foils are commercially available from Oak Mitsui under the trade name "TOC-500", "TOC-500-MLS", and "TOC-500-LZ", from Nippon Denkai under the trade name "USLP", and from Furukawa under the trade name "F1WS". High profile copper foils are commercially available from Circuit Foil under the trade name "TWS."

Suitable dielectric circuit substrates comprise low polarity, low dielectric constant and low loss resins, including those based on thermosetting resins such as 1,2-polybutadiene, polyisoprene, poly(etherimide) (PEI), polybutadiene-polyisoprene copolymers, poly(phenylene ether) resins, and those based on allylated poly(phenylene ether) resins. These materials, while exhibiting the desirable features of low dielectric constant and low loss, also exhibit low copper peel strength. The copper peel strength of such materials can be significantly improved by the use of the instant invention. It is also important that the peel strength remain relatively high at elevated temperatures to allow for "rework," i.e., the removal and replacement of soldered components on the circuit board. Combinations of low polarity resins with higher polarity resins can also be used, non-limiting examples including epoxy and poly(phenylene ether), epoxy and poly(ether imide), cyanate ester and poly(phenylene ether), and 1,2-polybutadiene and polyethylene. Compositions containing polybutadiene, polyisoprene, and/or butadiene- and isoprene-containing copolymers are especially useful.

Particularly suitable circuit substrates are thermosetting compositions comprising a thermosetting polybutadiene and/or polyisoprene resin. As used herein, the term "thermosetting polybutadiene and/or polyisoprene resin" includes homopolymers and copolymers comprising units derived from butadiene, isoprene, or mixtures thereof. Units derived from other copolymerizable monomers can also be present in the resin, for example in the form of grafts. Exemplary copolymerizable monomers include, but are not limited to, vinylaromatic monomers, for example substituted and unsubstituted monovinylaromatic monomers such as styrene, 3-methylstyrene, 3,5-diethylstyrene, 4-n-propylstyrene, alpha-methylstyrene, alpha-methyl vinyltoluene, para-hydroxystyrene, para-methoxystyrene, alpha-chlorostyrene, alpha-bromostyrene, dichlorostyrene, dibromostyrene, tetrachlorostyrene, and the like; and substituted and unsubstituted divinylaromatic monomers such as divinylbenzene, divinyltoluene, and the like. Combinations comprising at least one of the foregoing copolymerizable monomers can also be used. Exemplary thermosetting polybutadiene and/or polyisoprene resins include, but are not limited to, butadiene homopolymers, isoprene homopolymers, butadiene-vinylaromatic copolymers such as butadiene-styrene, isoprene-vinylaromatic copolymers such as isoprene-styrene copolymers, and the like.

The thermosetting polybutadiene and/or polyisoprene resins can also be modified, for example the resins can be hydroxyl-terminated, methacrylate-terminated, carboxylate-terminated resins. Post-reacted resins can be used, such as such as epoxy-, maleic anhydride-, or urethane-modified butadiene or isoprene resins. The resins can also be crosslinked, for example by divinylaromatic compounds such as divinyl benzene, e.g., a polybutadiene-styrene crosslinked with divinyl benzene. Suitable resins are broadly classified as "polybutadienes" by their manufacturers, for example Nippon Soda Co., Tokyo, Japan, and Sartomer Company Inc., Exton, Pa. Mixtures of resins can also be used, for example, a mixture of a polybutadiene homopolymer and a poly (butadiene-isoprene) copolymer. Combinations comprising a syndiotactic polybutadiene can also be useful.

The thermosetting polybutadiene and/or polyisoprene resin can be liquid or solid at room temperature. Suitable liquid resins can have a number average molecular weight greater than about 5,000 but generally have a number average molecular weight of less than about 5,000 (most preferably about 1,000 to about 3,000). Thermosetting polybutadiene and/or polyisoprene resins having at least 90 wt % 1,2 addition are preferred because they exhibit the greatest crosslink density upon cure, due to the large number of pendent vinyl groups available for crosslinking.

The polybutadiene and/or polyisoprene resin is present in the resin system in an amount of up to 100 wt %, specifically about 60 wt % with respect to the total resin system, more specifically about 10 to about 55 wt %, even more specifically about 15 to about 45 wt %, based on the total resin system.

Other polymers that can co-cure with the thermosetting polybutadiene and/or polyisoprene resins can be added for specific property or processing modifications. For example, in order to improve the stability of the dielectric strength and mechanical properties of the electrical substrate material over time, a lower molecular weight ethylene propylene elastomer can be used in the resin systems. An ethylene propylene elastomer as used herein is a copolymer, terpolymer, or other polymer comprising primarily ethylene and propylene. Ethylene propylene elastomers can be further classified as EPM copolymers (i.e., copolymers of ethylene and propylene monomers) or EPDM terpolymers (i.e., terpolymers of ethylene, propylene, and diene monomers). Ethylene propylene diene terpolymer rubbers, in particular, have saturated main chains, with unsaturation available off the main chain for facile cross-linkin. Liquid ethylene propylene diene terpolymer rubbers, in which the diene is dicyclopentadiene, are preferred.

Useful molecular weights of the ethylene propylene rubbers are less than 10,000 viscosity average molecular weight. Suitable ethylene propylene rubbers include an ethylene propylene rubber having a viscosity average molecular weight (MV) of about 7,200, which is available from Uniroyal Chemical Co., Middlebury, Conn., under the trade name Trilene CP80; a liquid ethylene propylene dicyclopentadiene terpolymer rubbers having a molecular weight of about 7,000, which is available from Uniroyal Chemical Co. under the trade name of Trilene 65; and a liquid ethylene propylene ethylidene norbornene terpolymer, having a molecular weight of about 7,500, which is available from Uniroyal Chemical Co. under the name Trilene 67.

The ethylene propylene rubber is preferably present in an amount effective to maintain the stability of the properties of the substrate material over time, in particular the dielectric strength and mechanical properties. Typically, such amounts are up to about 20 wt % with respect to the total weight of the resin system, more specifically about 4 to about 20 wt %, even more specifically about 6 to about 12 wt %.

Another type of co-curable polymer is an unsaturated polybutadiene- or polyisoprene-containing elastomer. This component can be a random or block copolymer of primarily 1,3-addition butadiene or isoprene with an ethylenically unsaturated monomer, for example a vinylaromatic compound such as styrene or alpha-methyl styrene, an acrylate or methacrylate such a methyl methacrylate, or acrylonitrile. The elastomer is preferably a solid, thermoplastic elastomer comprising a linear or graft-type block copolymer having a polybutadiene or polyisoprene block, and a thermoplastic block that preferably is derived from a monovinylaromatic monomer such as styrene or alpha-methyl styrene. Suitable block copolymers of this type include styrene-butadiene-styrene triblock copolymers, for example those available from Dexco Polymers, Houston, Tex., under the trade name Vector 8508M, from Enichem Elastomers America, Houston, Tex., under the trade name Sol-T-6302, and those from Fina Oil and Chemical Company, Dallas, Tex., under the trade name Finaprene 401; styrene-butadiene diblock copolymers; and mixed triblock and diblock copolymers containing styrene and butadiene, for example those available from Shell Chemical Corporation, Houston, Tex., under the trade name Kraton D1118. Kraton D1118 is a mixed diblock/triblock styrene and butadiene containing copolymer, containing 30 volume % styrene.

The optional polybutadiene- or polyisoprene-containing elastomer can further comprise a second block copolymer similar to that described above, except that the polybutadiene or polyisoprene block is hydrogenated, thereby forming a polyethylene block (in the case of polybutadiene) or an ethylene-propylene copolymer block (in the case of polyisoprene). When used in conjunction with the above-described copolymer, materials with greater toughness can be produced. An exemplary second block copolymer of this type is Kraton GX1855 (commercially available from Shell Chemical Corp.), which is believed to be a mixture of a styrene-high 1,2-butadiene-styrene block copolymer and a styrene-(ethylene-propylene)-styrene block copolymer. Another exemplary block copolymer is Kraton G (commercially available also from Shell Chemical Corp.), a maleic anhydride modified block copolymer of styrene-ethylene-butylene-styrene.

Typically, the unsaturated polybutadiene- or polyisoprene-containing elastomer component is present in the resin system in an amount of about 10 to about 60 wt % with respect to the total resin system, more specifically about 20 to about 50 wt %, or even more specifically about 25 to about 40 wt %.

Still other co-curable polymers that can be added for specific property or processing modifications include, but are not limited to, homopolymers or copolymers of ethylene such as polyethylene and ethylene oxide copolymers; natural rubber; norbornene polymers such as polydicyclopentadiene; hydrogenated styrene-isoprene-styrene copolymers and butadiene-acrylonitrile copolymers; unsaturated polyesters; and the like. Levels of these copolymers are generally less than 50 vol. % of the total resin system.

Crosslinking agents can optionally be added to increase the crosslink density of the resin(s). Examples of cross-linking agents include, without limitation, triallylisocyanurate, triallylcyanurate, diallyl phthalate, divinyl benzene, and multifunctional acrylate monomers (e.g., the Sartomer resins available from Arco Specialty Chemicals Co.), and combinations thereof, all of which are commercially available, with triallylisocyanurate being particularly exemplary. The cross-linking agent content of the thermosetting composition can be readily determined by one of ordinary skill in the art, depending upon the desired flame retardancy of the composition, the amount of the other constituent components, and the other properties desired in the final product. UL-94, an Underwriters Laboratories flammability test, provides four possible ratings, HB, V-2, V-1, and V-0. V-0 is the most difficult rating to obtain, requiring that five bars of material self extinguish with an average flame out time of five seconds or less without dripping. More particularly, the amount of cross-linking agent depends upon the loading of magnesium hydroxide and amount(s) of the other components in the thermosetting composition, and attaining excellent flame retardancy, electrical and moisture properties, all of which will be described in greater detail below. When used to increase the crosslink density, effective quantities are greater than or equal to about 0.5 wt %, specifically greater than or equal to about 1 wt %, and more specifically greater than or equal to about 5 wt % based on the total weight of the thermosetting composition. Effective quantities can be less than about 10 wt %, specifically about 10 wt %, and more specifically less than about 7 wt. %.

Particulate fluoropolymers can optionally be included in the thermosetting composition. Exemplary particulate fluoropolymers include those known in the art for use in circuit subassemblies, and include but are not limited to fluorinated homopolymers, for example polytetrafluoroethylene (PTFE), and fluorinated copolymers, e.g., copolymers of tetrafluoroethylene with hexafluoropropylene or perfluoroalkylvinylethers such as perfluorooctylvinyl ether, or copolymers of tetrafluoroethylene with ethylene. Blends of fluorinated polymers, copolymers, and terpolymers can also be used. The fluoropolymers can be in fine powder, dispersion, or granular form, including fine powder (or "coagulated dispersion") PTFE, made by coagulation and drying of dispersion-manufactured PTFE, generally manufactured to exhibit a particle size of about 400 to about 500 micrometers; granular PTFE made by suspension polymerization, generally having two different particle size ranges (median particle size of about 30 to about 40 micrometers for the standard product, and about 400 to about 500 micrometers for the high bulk density product); and/or granular PTFE, FEP, or PFA. The granular fluoropolymers can be cryogenically ground to exhibit a median particle size of less than about 100 micrometers.

When present, the effective particulate fluoropolymer content of the thermosetting composition can be readily determined by one of ordinary skill in the art, depending upon the desired flame retardancy of the composition, the amount of the other components, and the other properties desired in the final product. More particularly, the amount of the fluoropolymer composition depends upon the loading of magnesium hydroxide and amount(s) of other flame retardants in the thermosetting composition. In general, effective quantities are greater than or equal to about 1 to about 90 parts by weight per hundred parts by weight of the other thermosetting polymer components (phr), specifically about 5 to about 75 phr, and most specifically about 10 to about 50 phr (parts per hundred parts by weight) of the total thermosetting resin composition.

A curing agent can be added to the resin system to accelerate the curing reaction of the polyenes having olefinic reactive sites. Specifically useful curing agents are organic peroxides such as, dicumyl peroxide, t-butyl perbenzoate, 2,5-dimethyl-2,5-di(t-butyl peroxy)hexane, α,α-di-bis(t-butyl peroxy)diisopropylbenzene, and 2,5-dimethyl-2,5-di(t-butyl peroxy) hexyne-3, all of which are commercially available. They can be used alone or in combination. Typical amounts of curing agent are from about 1.5 to about 10 wt % of the total resin composition.

The circuit substrate materials can optionally include particulate fillers. Examples of suitable fillers include titanium dioxide (rutile and anatase), barium titanate, strontium titanate, silica (particles and hollow spheres) including fused amorphous silica; corundum, wollastonite, aramide fibers (e.g., Kevlar), fiberglass, $Ba_2Ti_9O_{20}$, glass spheres, quartz, boron nitride, aluminum nitride, silicon carbide, beryllia, alumina, magnesia, mica, talcs, nanoclays, aluminosilicates (natural and synthetic), and magnesium hydroxide. Combinations of fillers can also be used. More specifically, rutile titanium dioxide and amorphous silica are especially desirable because these fillers have a high and low dielectric constant, respectively, thereby permitting a broad range of dielectric constants combined with a low dissipation factor to be achieved in the final cured product by adjusting the respective amounts of the two fillers in the composition. These fillers can be used alone or in combination.

The circuit substrate can optionally further include woven, thermally stable webs of a suitable fiber, specifically glass (E, S, and D glass), including flat glass or close-weaved fiber glass, or high temperature polyester fibers (e.g., KODEL from Eastman Kodak). Such thermally stable fiber reinforcement provides a circuit laminate with a means of controlling shrinkage upon cure within the plane of the laminate. In addition, the use of the woven web reinforcement renders a circuit substrate with a relatively high mechanical strength.

Examples of the woven fiberglass web are set forth in Table 1.

TABLE 1

| Manufacturer | Style | Thickness, in. (um) |
|---|---|---|
| Fiber Glast | 519-A | 0.0015 (38.1) |
| Clark-Schwebel | 112 | 0.0032 (81.3) |
| Clark-Schwebel | 1080 | 0.0025 (63.5) |
| Clark-Schwebel | 1674 | 0.004 |
| Burlington | 7628 | 0.0068 (172.7) |
| JPS Composite Materials | 106 | 0.0013 |
| JPS Composite Materials | 3313 | 0.0033 |
| JPS Composite Materials | 1067 | 0.0014 |
| JPS Composite Materials | 1280 | — |

The thermosetting composition, having particular utility as a substrate for an electrical circuit material, further comprises about 50 to about 80 percent by weight, based on the total weight of the composition, of magnesium hydroxide having a low ionic content. The inventors have discovered that the use of magnesium hydroxide having low ionic content as a flame retardant allows the circuit substrate to achieve the desired flame retardance rating of at least UL94 V-1 in the absence of halogenated flame retardants, particularly brominated flame retardants, while retaining low dielectric loss and good thermal stability.

A number of commercially available magnesium hydroxides can be suitable for use in the present thermosetting compositions, for example those available under the trade name MAGNIFIN® from Albemarle Corp. According to the product literature, MAGNIFIN® H51V and MAGNIFIN® H101V are magnesium hydroxides having a low ionic content, and are treated (coated) with an aminosilane. Low ionic content is herein defined as containing less than about 1,000 ppm, specifically less than about 500 ppm, by weight of ionic contaminants such as chloride ion. In addition, in an exemplary embodiment, the magnesium hydroxide has a low total metal content. A low total metal content is herein defined as less than about 500 ppm, specifically less than about 400 ppm, more specifically less than about 300 ppm, by weight of metal contaminants such as iron, aluminum, chromium, manganese, copper, and the like. In a specific embodiment the amount of iron oxide can be limited to less than about 100 ppm, preferably less than about 50 ppm. Other suitable magnesium hydroxides are commercially available under the trade name MGZ-6R from Sakai Chemicals, Japan, MAG-SHIELD from Martin Marietta Corp., ZEROGEN from J. M. Huber Engineering materials, and FR20 from Dead Sea Bromine Group.

In addition, the particulate size of the magnesium hydroxide can impact the electrical and flame retardant properties of the substrate material. The magnesium hydroxide can have an average surface area (BET) of about 2 to about 12 square meters per gram, specifically about 5 to about 10; and an average particle size of about 0.1 to about 2 micrometers. The magnesium hydroxide comprises about 50 to about 80 percent by weight of the total thermosetting composition (i.e., the resin system as described below, including curing agent, crosslinking agent, and magnesium hydroxide, but exclusive of any reinforcing glass web or filler).

In an optional embodiment, the magnesium hydroxide can be coated, i.e., surface treated. Examples of coated magnesium hydroxide can include silane coated magnesium hydroxide, silica coated magnesium hydroxide, alumina coated magnesium hydroxide, and combinations of the above, specifically silica-methyl hydrogen polysiloxane coated magnesium hydroxide. Examples of the surface-treating agent that can be used to form silica, alumina and/or silane coatings can include, without limitation, methyl hydrogen polysiloxane such as APS-219 from Advanced Polymers Inc., MH1107 Fluid from Dow Corning, silane coupling agents such as vinyltrichlorosilane, vinyltrimethoxysilane, vinyltriethoxysilane, vinyltris(β-methoxyethoxy)silane, β-(3,4-epoxycyclohexyl)ethyltrimethoxysilane, γ-glycidoxypropyltrimethoxysilane, γ-glycidoxypropylmethyldiethoxysilane, γ-glycidoxypropyltriethoxysilane, γ-methacryloxypropylmethyldimethoxysilane, γ-methacryloxypropyltrimethoxysilane, γ-methacryloxypropylmethyldiethoxysilane, γ-methacryloxypropyltriethoxysilane, N-β(aminoethyl)γ-aminopropylmethyldimethoxysilane, N-β(aminoethyl)γ-aminopropyltrimethoxysilane, N-β(aminoethyl)γ-aminopropyltriethoxysilane, γ-aminopropyltrimethoxysilane, γ-aminopropyltriethoxysilane, N-phenyl-γ-aminopropyltrimethoxysilane and γ-mercaptopropyltrimethoxysilane. An exemplary silica coated magnesium hydroxide is a silica coated magnesium hydroxide having an average particle size in the range of 1.5-2.5 micrometers and a surface area of about 3 to about 10 meter per square gram available from Sakai Chemicals, Japan, under the trade name MGZ-6R. An exemplary silane coated magnesium hydroxide is a silane coated magnesium hydroxide having a particle size of about 2.25 micrometers and a surface area of about 3-4 meter square per gram available from Kisuma Chemicals, Japan, under the trade name Kisuma 8SN. Other specialty coatings for magnesium hydroxide particles include fatty acids, zinc hydroxide, and combinations of these with silane or silica. Other coated magnesium hydroxides are Kisuma 5N and 5J from Kyowa Chemical, Magseeds EP1-A and EN1 from Knoshima Chemical, and Ecomag PZ-1EX and Z-10 from Tatebo Industries.

As described, use of magnesium hydroxide can eliminate the need for a halogenated flame retardant. However, in order to obtain a sufficient non-flammable property for the circuit subassembly, a great amount thereof needs to be added to the thermosetting resin, with the result that the other properties of the circuit could deteriorate. In the extreme, porosity can be a result of high magnesium hydroxide loadings. Such high magnesium hydroxide loading can cause the problems of increased water absorption, which negatively affects electrical properties, decreased acid resistance, which reduces the ability to fabricate fine line conductor patterns, and increased absorption of solvents and other circuit fabrication solutions, which can lead to electrical and other performance problems in the resulting circuit.

In an optional embodiment, the circuit subassembly can further comprise one or more other additives. These other additives can allow a reduction in the amount of magnesium hydroxide used and can, in cases, reduce the overall loading of additives in the circuit subassembly while still achieving a UL94 rating of at least V-1 without the use of halogens. Importantly, the combination of reduced magnesium hydroxide and the other additives can give significant improvements in the important circuit material properties of water absorption, solvent absorption, acid resistance, and adhesion between the circuit substrate and a conductive metal.

Effective other additives for use with magnesium hydroxide are compounds containing a high percentage of nitrogen in their molecular structure. Specifically, effective other additives can be compounds containing greater than about 20% nitrogen. The magnesium hydroxide and high nitrogen-containing compound act synergistically with regard to flame retardance, with a resulting unexpected improvement in other properties. It can also be that the combination of different additives disperses and packs better than magnesium hydroxide alone.

Examples of such nitrogen-containing compounds can include, without limitation, triazines, guanidines, cyanurates, isocyanurates, ammonium polyphosphates, phosphazene, silazane and its polymer, melamine based resins, and the like, and mixtures thereof. Examples of triazines can include melamine, Melam, Melem, Melon, ammeline, ammelide, ureidomelamine, acetoguanamine, benzoguanamine, and the like. Triazines can further include salts and adducts of these compounds with boric acid, phosphoric acid. Examples include melamine phosphate, melamine pyrophosphate, and melamine polyphosphate. Examples of guanidine compounds can include guanidine, aminoguanidine, and the like; and their salts and adducts with boric acid, carbonic acid, phosphoric acid, nitric acid, sulfuric acid, and the like; and mixtures thereof. Examples of cyanurate and isocyanurate compounds can include the salts and adducts of the triazine compounds with cyanuric acid and isocyanuric acid, such as melamine cyanurate, melamine isocyanurate, and hydroxyl-ethyl isocyanurate triacrylate. The nitrogen-containing compounds are known in the art, as are methods for their preparation, and many are commercially available.

As noted, the addition of high nitrogen containing compounds to replace a portion of the magnesium hydroxide results in the halogen-free circuit subassembly composition of this disclosure with an excellent combination of properties.

One noted improvement is in acid resistance. This improvement is measured by acid weight loss. A significance of the improvement is to improve resistance to degradation during electroless nickel-immersion gold (ENIG) processing. Another area of improvement is in lower solvent absorption and lower porosity. This improvement can be measured by xylene absorption. Yet another improvement is increased bond between the dielectric of the substrate and a low profile copper foil conductive layer.

The optional nitrogen-containing compounds generally contain about 15 to about 65% by weight nitrogen. These compounds are used in combination with magnesium hydroxides in a preferred concentration of about 4 to about 25% based on the weight of magnesium hydroxide. Less than about 4% can not be effective in achieving desired flame retardance and greater than about 25% could result in excessive porosity and higher dissipation factor.

In an optional exemplary embodiment the thermosetting resin composition of the circuit subassemblies can comprise a melamine cyanurate or a melamine polyphosphate nitrogen-containing additive. An exemplary melamine cyanurate compound has a nitrogen content of equal to or greater than about 40 percent by weight and is available from Ciba Specialty Chemicals, Basel, Switzerland, under the trade name MC-15. An exemplary melamine polyphosphate compound has a nitrogen content of equal to or greater than about 40 percent by weight and is available from Ciba Specialty Chemicals, Basel, Switzerland, under the trade name Melapur 2000.

Also, like the magnesium hydroxide flame retardant, the nitrogen compound can be coated with silica, fatty acid, silanes, silica-silanes, alumina, alumina-silica, alumina-silica-silanes, and the like. An exemplary coated melamine polyphosphate has a nitrogen content of equal to or greater than 40% by weight and is available from Flame Chk Inc. under the trade name Budit 3141CA. Use of such exemplary nitrogen-containing compounds can result in the reduction of about 20 to about 40 percent by weight of magnesium hydroxide from the thermoset resin composition, while maintaining the desired flame retardant properties.

When present in the thermosetting composition, the nitrogen-containing compound can be used in an amount of about 4 to about 20 percent by weight, based on the weight total of the thermosetting composition. An exemplary weight % range of the nitrogen-containing compound is about 5 to about 15%, specifically about 6 to about 12%.

In one embodiment, the composition comprises the magnesium hydroxide flame retardant and the nitrogen-containing compound. In this embodiment, the weight ratio of the magnesium hydroxide flame retardant to the nitrogen-containing compound can be about 3:1 to about 25:1, specifically about 4:1 to about 15:1, and more specifically about 5:1 to about 10:1.

Turning now to a method of forming the circuit subassembly, the adhesive composition can be directly applied to a conductive layer or a dielectric substrate layer as a coating (if of sufficiently low viscosity), or dissolved or suspended, i.e., in the form of a solution. Where a solution is used, the adhesive composition is dissolved in a suitable solvent before application. The solvent is chosen so as to dissolve the adhesive composition and to have a convenient evaporation rate for applying and drying the coating. A non-exclusive list of possible solvents is xylene, toluene, methyl ethyl ketone, methyl isobutyl ketone, hexane, and higher liquid linear alkanes, such as heptane, octane, nonane, and the like, cyclohexane, isophorone, and various terpene-based solvents. Specifically, suitable solvents include xylene, toluene, methyl ethyl ketone, methyl isobutyl ketone, and hexane, and more specifically xylene and toluene. The concentration of the adhesive composition in solution is not critical and will depend on the solubility of the adhesive components, the method of application, and other factors. In general, the solution comprises 1 to about 50 wt %, more specifically about 5 to about 20 wt % of the adhesive composition, based on the total weight of the adhesive solution.

The adhesive or adhesive solution can be applied to a surface of a conductive layer or a dielectric circuit substrate material (e.g., a prepreg or a B-staged material) by known methods in the art, for example by dip, spray, wash, or other suitable coating technique. If the adhesive solution exhibits phase separation during coating or drying, the uniformity can be improved by increasing the solution temperature. Where a solvent is present, the adhesive solution is allowed to dry under ambient conditions, or by forced or heated air, to form an adhesion promoting layer. Typically, the adhesion promoting layer is applied to provide a coating weight of about 2 grams per square meter (g/m² or "gsm") to about 15 g/m², specifically about 3 g/m² to about 8 g/m². The adhesion promoting layer can be uncured or partially cured in the drying process, or the adhesion promoting layer can be partially or fully cured, if desired, after drying.

After application of the adhesive coating, the coated conductive layer or coated circuit substrate can be stored or used directly to form a circuit laminate. The laminate can be formed by means known in the art. In one embodiment, the lamination process entails placing one or more layers of coated or uncoated circuit substrate between one or two sheets of coated or uncoated conductive layers (provided that an adhesive layer is disposed between at least one conductive layer and at least one dielectric substrate layer). The layered material can then be stored prior to lamination and cure, partially cured and then stored, or laminated and cured after stacking. Lamination and curing can be by a one-step process, for example using a vacuum press, or by a multiple-step process. In an exemplary multiple-step process, a conventional peroxide cure step at temperatures of about 150° C. to about 200° C. is conducted, and the partially cured stack can then be subjected to a high-energy electron beam irradiation cure (E-beam cure) or a high temperature cure step under an inert atmosphere. Use of a two-stage cure can impart an unusually high degree of cross-linking to the resulting laminate. The temperature used in the second stage is typically about 250° C. to about 300° C., or the decomposition temperature of the resin. This high temperature cure can be carried out in an oven but can also be performed in a press, namely as a continuation of the initial lamination and cure step. Particular lamination temperatures and pressures will depend upon the particular adhesive composition and the substrate composition, and are readily ascertainable by one of ordinary skill in the art without undue experimentation.

In accordance with various specific embodiments, FIG. 1 shows an exemplary circuit material 10 comprising adhesive layer 14 disposed on a conductive layer, e.g., a copper foil 12. As used herein, "disposed" means at least partial intimate contact between conductive layer copper foil and the adhesive. It is to be understood that in all of the embodiments described herein, the various layers can fully or partially cover each other, and additional copper foil layers, patterned circuit layers, and dielectric layers can also be present. Adhesive layer 14 can be uncured or partially cured.

Figure 2:
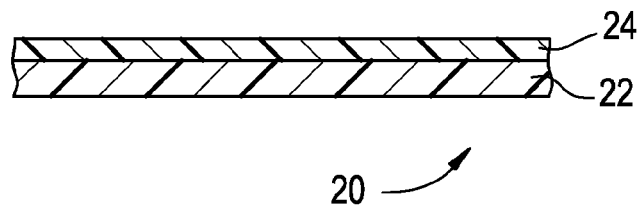
FIG. 2 shows an exemplary circuit subassembly with an adhesive layer disposed on a dielectric substrate layer.

FIG. 2 shows an exemplary circuit material 20 comprising an adhesive layer 24 disposed on a dielectric circuit substrate 22. Adhesive layer 24 can be uncured or partially cured, and substrate 22 can be uncured, partially cured, or fully cured.

Figure 3:
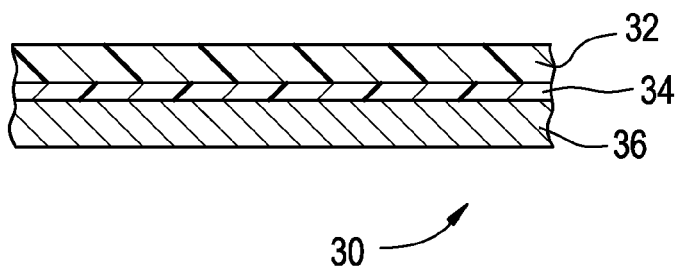
FIG. 3 shows an exemplary circuit laminate comprising an adhesive layer.

FIG. 3 shows an exemplary circuit laminate 30 comprising an adhesive layer 34 disposed between a dielectric circuit substrate 32 and a conductive layer 36, e.g., a copper foil. Adhesive layer 34 can be uncured or partially cured, and substrate 32 can be uncured, partially cured, or fully cured.

Figure 4:
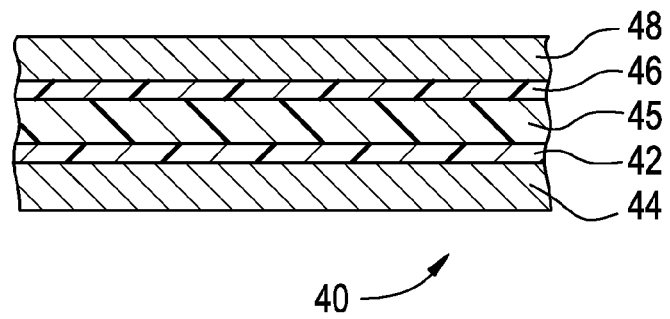
FIG. 4 shows an exemplary double clad circuit laminate comprising two adhesive layers.

FIG. 4 shows an exemplary double clad circuit laminate 40 comprising a first adhesive layer 42 disposed between a first conductive layer 44 and a first side of a dielectric circuit substrate 45. Second adhesive layer 46 is disposed between second conductive layer 48 and a second side of circuit substrate 45. The first and second adhesive layers 42, 46 can comprise the same or different polymer composition, and first and second conductive layers 44, 48 can comprise the same or different types of conductive layer, e.g. copper foil. It is also possible to use only one of the adhesive layers 42, 46, or to substitute one of adhesive layers 42, 43 with a bond ply as is known in the art (not shown).

Figure 5:
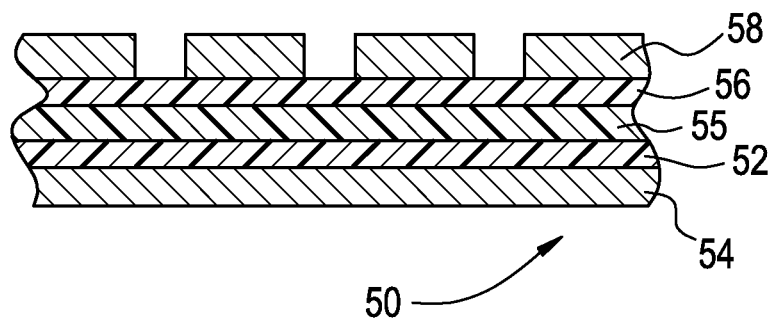
FIG. 5 shows an exemplary double clad circuit comprising two adhesive layers.

FIG. 5 shows an exemplary double clad circuit 50 comprising a first adhesive layer 52 disposed between a first conductive layer 54 and a first side of a dielectric circuit substrate 55. Second adhesive layer 56 is disposed between a patterned (e.g., etched) circuit layer 58 and a second side of dielectric circuit substrate 55. The first and second adhesive layers 52, 56 can comprise the same or different polymer composition. It is also possible to use only one of the adhesive layers 52, 56, or to substitute one of adhesion layers 52, 56 with a bond ply as is known in the art (not shown).

Figure 6:
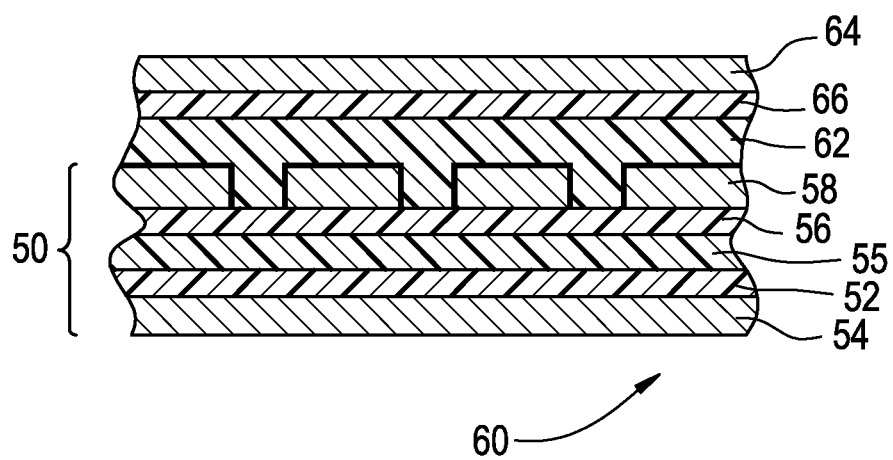
FIG. 6 shows an exemplary multi-layer circuit comprising three adhesive layers.

FIG. 6 shows an exemplary circuit 60 comprising the circuit material 50 as described in FIG. 5. A bond ply 62 can be disposed on the side of the patterned circuit 58 opposite adhesive layer 56, and resin-coated conductive layer comprising a copper foil 64 disposed on bond ply 62 is disposed on a side opposite patterned circuit 58. Optionally, and as shown in FIG. 6, a third adhesive layer 66 is disposed between bond ply 62 and copper foil 64. The first, second, and third adhesive layers 52, 56, 62, can comprise the same or different polymer composition, and first and second conductive layers 54, 64 can comprise the same or different types of, e.g., copper foil.

The circuit subassemblies, which are halogen-free and can have a bond improving coating, when combined, give circuit materials having numerous advantages. The subassemblies can have a UL94 rating of at least V-1 without the use of brominated flame retardants. In addition, they have low water absorption, generally less than about 0.5%, specifically less than about 0.3%. Bond strength of low profile copper foil to the coated circuit subassembly is generally greater than about 5.0 pounds per linear inch (pli). Resistance to the acids and other solutions used in circuit fabrication is high. In addition, electrical and thermal properties are consistent with those desired in circuits for modern electrical and electronic applications, particularly a dissipation factor of less than about 0.006.

The invention is further illustrated by the following non-limiting Examples.

EXAMPLES

The materials listed in Table 2 were used in the following examples.

TABLE 2

| Material name | Chemical name | Supplier |
|---|---|---|
| PPE-MA | Maleinized polyphenylene ether | Asahi |
| Blendex HPP820 | Unmodified polyphenylene ether | Chemtura |
| Ricon ® 184MA6 | Butadiene-styrene copolymer adducted with maleic anhydride | Sartomer |
| Ricon 257 | Styrene-butadiene-divinyl benzene polymer | Sartomer |
| Hycar 2000 X168 | Carboxy polybutadiene | Noveon |
| TE 2000 | Polybutadiene with urethane linkages | Nippon Soda |
| B3000 | Vinyl-terminated polybutadiene | Nippon Soda |
| BN1015 | Maleinated polybutadiene | Nippon Soda |
| JSR 810 | Syndiotactic polybutadiene | JSR Corporation |
| Kraton ® D-1118 | SB diblock copolymer (20%) and SBS triblock copolymer (80%) | Kraton Polymers |
| RO-4350B | Flame retardant thermosetting hydrocarbon-based circuit substrate material | Rogers Corp. |
| RO-4233 | Thermosetting hydrocarbon-based circuit substrate material | Rogers Corp. |
| FR | Flame retardant nonpolar circuit substrate material containing $Mg(OH)_2$ (U.S. Pat. No. 7,022,404 to Sethumadhavan et al.) | |
| TOC-500 | Low profile standard copper, zinc free | Oak-Mitsui |
| TOC-500-LZ | Low profile copper, with light zinc flush | Oak-Mitsui |
| TWS | High profile copper foil | Circuit Foil |
| A74NT | Aminosilane | Gelest, Inc. |
| Trilene 65 | Ethylene propylene diene monomer liquid rubber | Crompton Corp. |
| MGZ-6R | Silica coated magnesium hydroxide | Sakai Chemicals |
| MGZ-6R-2 | Higher density silica coated magnesium hydroxide | Sakai Chemicals |
| CE 44I | Fused silica | C.E. Minerals |
| CE 44IR | Fused silica | C.E. Minerals |
| BA 188 | Fused silica | Brook Services Inc. |
| Naugard XL | Antioxidant for rubber | Crompton Corp. |
| Perkadox 30 | 2,3-Dimethyl-2,3-diphenylbutane curing agent | Akzo Nobel |
| TAIC | Triallyl isocyanurate | |
| Varox | Peroxide curing agent | RT Vanderbilt |
| MC-15 | Melamine cyanurate | Ciba |
| Budit 315, 3141CA | Melamine cyanurate | Flame CHK Inc |
| Melapur 200 | Melamine polyphosphate | Ciba |
| Kisuma 8SN | Silane coated magnesium hydroxide | Kyowa Chemicals |

Copper peel strength was tested in accordance with the "Peel strength of metallic clad laminates" test method (IPC-TM-650 2.4.8).

The laminates were tested for solder float by floating them on a pot of molten solder at a temperature of 288° C. for 10 seconds. This procedure is repeated five times on each sample. A failure in the solder float test is noted if there is blistering or delamination of the copper foil from the laminate surface.

Examples 1-4 and Comparative Examples A-D

Circuit laminates were prepared using an adhesive composition as set forth in Table 3 disposed between a dielectric circuit substrate and a copper foil. The adhesive compositions in Examples 1, 1A-4 and A-D contained 100 parts by weight of a maleinized poly(arylene ether) (10 wt % solution in a solvent having 98% toluene and 2% xylene), 0.5 parts by weight of Varox (a peroxide cure initiator), and the indicated amounts of a functionalized polybutadiene polymer and an elastomeric block copolymer.

The adhesive was coated onto ½ oz./ft² TWS copper foil with an RMS surface roughness of greater than 2 um, as measured by the WYCO interferometer, and dried to provide a coating having dry coating basis weight of 5-6 g/m². Prepreg sheets of two different dielectric substrates were laminated to the treated copper foil using a press cycle consisting of a rapid ramp to 345° F. (174° C.) and 15 minute hold at 345° F. (174° C.) and then a ramp to 475° F. (246° C.) and an additional hour hold at 475° F. (246° C.). A pressure of 1000 psi (70.3 kilogram/centimeters²) is maintained throughout the cycle.

The samples were tested for solder float and if they passed, they were subsequently tested for peel strength. Results are shown in Table 3.

TABLE 3

| Component | Ex. 1 | Ex. 1A | Ex. 2 | Ex. 3 | Ex. 4 | Ex. A | Ex. B | Ex. C | Ex. D |
|---|---|---|---|---|---|---|---|---|---|
| PPE-MA solution | 100 | 100 | 100 | 100 | 100 | 100 | 100 | 100 | 100 |
| KRATON D-1118 | 7.5 | 7.5 | 7.5 | 7.5 | 12.0 | 7.5 | 7.5 | 7.5 | — |
| B3000 | — | 7.5 | — | — | — | — | — | — | — |
| RICON 184MA6 | 3.5 | — | 7.5 | 10.0 | 7.5 | — | — | — | — |
| Hycar 2000 X168 | — | — | — | — | — | — | — | 7.5 | — |
| TE 2000 | — | — | — | — | — | — | — | — | 7.5 |

TABLE 3-continued

| Component | Ex. 1 | Ex. 1A | Ex. 2 | Ex. 3 | Ex. 4 | Ex. A | Ex. B | Ex. C | Ex. D |
|---|---|---|---|---|---|---|---|---|---|
| Solder Float, 288° C. (pass/fail) | Marginal | Marginal | Pass | Pass | Pass | Fail | Fail | Fail | Fail |
| Bond with FR substrate (pli) | NT | NT | 5.3 | 4.0 | 5.6 | NT | NT | NT | NT |
| Bond with RO 4350B (pli) | NT | 4.51 | 5.4 | NT | NT | NT | NT | NT | NT |

NT—not tested.

These examples demonstrate that an adhesive in accordance with the present invention increases copper peel strength of a circuit laminate having a comparatively high profile foil. They also demonstrate the efficacy of the coating in improving adhesion to substrate compositions other than RO4350B high frequency laminate. Furthermore, they demonstrate the importance of the maleinized polybutadiene in improving the high temperature resistance of the adhesive coating.

Comparative Examples A and D show that with the three components of the adhesive composition used here, all three are required to simultaneously increase the copper peel strength and pass the high temperature solder float test. In particular, absence of the elastomeric block copolymer (Ex. D) and/or the carboxylated polybutadiene polymer (Exs. A-D) result in failure in solder float test. Substitution of a vinyl-terminated butadiene polymer (Ex. B) or a urethane-functionalized butadiene polymer (Ex. C) also results in failure in solder float test.

Examples 1-4 show that lower amounts of carboxylated butadiene polymer (Ex. 1) result in only marginal solder behavior, but that as the content of carboxylated butadiene polymer is increased, both satisfactory solder behavior and improved bonding were obtained (Exs. 2 and 4). Further increase in the carboxylated butadiene polymer (7.5 parts in Ex. 2 to 10.0 parts in Ex. 3) resulted in a slight decrease in copper peel strength (5.3 pli in Ex. 2 vs. 4.0 pli in Ex. 3). These examples demonstrate the utility of this coating to materials other than RO4350B circuit substrate.

Examples 2-4 were laminated to a halogen-free flame retardant $Mg(OH)_2$-filled material described in U.S. Pat. No. 7,022,404 to Sethumadhavan et al. Examples 2-4 demonstrate the utility of this coating with materials other than RO4350B circuit substrate. As a comparison, absence of any adhesive yields a bond strength of only 1.9 pli with the halogen-free system and about 3.5 pli with RO4350B circuit substrate.

The adhesive composition of Example 2 was also coated on two types of comparatively low profile electrodeposited copper foil (Oak Mitsui SQ-VLP and TQ-VLP) and laminated to an RO4350B prepreg as described above. As shown below, the bond of both types of foil was substantially increased by the use of the coating. Both samples also passed the 288° C. solder float testing as follows.

| Copper foil Type | Peel strength (no adhesive) | Peel strength with Adhesive |
|---|---|---|
| SQ-VLP | 2.2 pli | 4.5 pli |
| TQ-VLP | 2.3 pli | 4.2 pli |

This example demonstrates that the coating is effective at improving the bond to a wide variety of copper foils.

Examples 5-6 and Comparative Example E

In Examples 5 and 6, an adhesive solution was formed using 10 parts by weight of a solution of a maleinized poly (arylene ether) (10 wt % in a solution of 98% toluene and 2% xylene), a maleinated polybutadiene (7.5 parts by weight), and an elastomeric block copolymer 7.5 parts by weight). The adhesive solution was used to form a laminate prepared with an RO4350B prepreg (6 layers) and a low profile 0.5 oz copper foil (MLS TOC-500 LZ). The copper foil side having the low zinc treatment was placed in contact with the adhesive layer.

The materials were all laminated in a vacuum press using a rapid ramp to 345° F. (174° C.) and 15 minute hold at 345° F. (174° C.), followed by a ramp to 475° F. (246° C.) and an additional hour hold at 475° F. (246° C.). A pressure of 1000 psi (70.3 kilogram/centimeters2) was maintained throughout the cycle.

The samples were tested for bond strength, solder float, dielectric constant, and dissipation factor. Results are shown in Table 4.

TABLE 4

| Property | Ex. 5 | Ex. 6 | Ex. E |
|---|---|---|---|
| Bond (⅛-inch) (pli) | 5.3 | 4.7 | 3.0 |
| Solder Float | Pass | Pass | Pass |
| Dielectric Constant at 10 Ghz | 3.51 | 3.53 | 3.53 |
| Dissipation Factor at 10 Ghz | 0.0040 | 0.0042 | 0.0042 |

The results in Table 4 show that the copper peel strengths achieved with the adhesive on zinc-coated, low profile copper foils (Exs. 5 and 6) were more than 50% higher than the value without the adhesive (Ex. E). Moreover, results from Examples 5, 6, and E indicate that use of adhesive coating did not negatively impact the high temperature solderability, dielectric constant, or dissipation factor of the laminates.

Examples 8-10 and Comparative Example G

In Examples 8-10, an adhesive solution comprising 10 parts by weight of a maleinized poly(arylene ether) (10 wt % in a solution of 98% toluene and 2% xylene), 7.5 parts by weight of a maleinated polybutadiene, and 7.5 parts by weight of an elastomeric block copolymer was used as an adhesive for a laminate prepared with an RO4233 prepreg (3 layers) and a 0.4 um RMS low profile copper foil (MLS TOC-500-LZ, 0.5 oz). The copper foil side having the zinc treatment was placed in contact with the adhesive layer. Different coating thicknesses were used for Examples 8-10 (amounts shown are on a dry weight basis). In Comparative Example G, no adhesive formulation was used.

The samples were laminated as described above. Test results are shown in Table 5.

TABLE 5

| Components | Ex. 8 | Ex. 9 | Ex. 10 | Ex. G |
|---|---|---|---|---|
| Coating Thickness (gsm) | 3.0 | 5.0 | 10.0 | (No Coating) |
| Bond (pli) | 4.25 | 4.10 | 4.00 | 2.60 |
| Solder Float | Pass | Pass | Pass | Pass |

Examples 8-10 show that the improvement in copper peel strength is seen over a wide range of coating weights (from 3.0 gsm (Ex. 8) to 5.0 gsm (Ex. 9) and 10.0 gsm (Ex. 10)). The wide range of coating weight did not adversely affect the high temperature solder resistance.

The adhesion of the copper foil of Example 9 and Comparative Example G was further tested by measuring the copper pull strength. The pull strength was measured on 0.090-inch (0.2286-centimeter) diameter pads, by soldering a copper wire to the pad and pulling the wire perpendicular to the surface of the laminate with a tensile testing machine. The pull strength is calculated by dividing the maximum recorded force by the area of the pad. The results for four individual pulls of each material, reported in units of psi, are shown in Table 6.

TABLE 6

| | Replicate 1 | Replicate 2 | Replicate 3 | Replicate 4 |
|---|---|---|---|---|
| Example 9 | 8.49 | 10.58 | 9.10 | 7.54 |
| Example G | 5.72 | 5.79 | 7.75 | 6.40 |

The data show that pull strengths in laminates using the inventive adhesive are much higher than those without the adhesive. These results suggest that adhesive coatings improved pull strengths of the coated samples as compared to non-coated materials.

Examples 11-16 and Comparative Examples H-Q

The following examples demonstrate that the adhesive composition is useful for increasing the copper peel strength with a low profile foil. They also demonstrate the efficacy of the coating in improving adhesion to polybutadiene and/or polyisoprene dielectric substrates.

Accordingly, circuit laminates were prepared using an adhesive composition disposed between a circuit substrate and a copper foil. The adhesive compositions are described in Table 7 below. The adhesive compositions in Examples 11-15 and Comparative Examples J-L comprised 100 parts by weight of maleinized poly(arylene ether) (10 wt % solution in 98% toluene and 2% xylene), 0.5 parts by weight of Varox (a peroxide cure initiator), and the indicated amounts of a functionalized polybutadiene polymer and an elastomeric block copolymer. In Example 16, Blendex HPP820, an unmodified poly(arylene ether) commercially available from Chemtura, was substituted for the maleinized poly(arylene ether). In Example N, BN1015, a maleinated polybutadiene polymer commercially available from Nippon Soda, was substituted for the RICON 184MA6.

The adhesive was coated onto ½-oz./ft$^2$ MLS TOC-500-LZ copper foil with an RMS surface roughness of about 0.4 um, as measured by the WYCO interferometer at a final target dry basis weight of approximately 5 grams/m$^2$ (gsm) using a #28 Mayer rod and allowed to air dry in a hood. In example Q, the copper foil was uncoated.

Six 0.0033-inch (0.00838-centimeter) thick prepreg sheets of the RO4350 circuit substrate were laminated to the indicated dried coated copper samples using the above-described lamination cycle to from a 0.020-inch (0.0508-centimeter) thick laminate. The laminates were tested for solder float. Results are shown in Table 7.

Examples 11-16 show that all of the examples containing a poly(arylene ether) are at least 40% higher in copper peel strength than the uncoated control, Example Q. This improvement in relatively smooth copper adhesion alone is a significant improvement in the utility of these circuit substrates. Comparative examples H, I, M, and N demonstrate that the presence of the maleinized poly(arylene ether) also provides an increase in peel strength. In none of these four cases, which contain the other components of the coating formulation but do not contain a maleinized poly(arylene ether) polymer, does the copper peel strength exceed 3.5 pli.

Comparative examples J and K demonstrate that presence of the maleinated polybutadiene further improves the utility of the coating by improving the high temperature solder resistance of the finished laminate. It can be seen from table 7 that all examples containing the maleinized or non-maleinized poly(arylene ether) that also contain the maleinated polybutadiene exhibit both the increase in copper peel strength and pass the 288° C. solder float test. Without being bound by theory, it is believed that the increased polarity of the maleinated polybutadiene polymer helps improve the high temperature bond of the copper foil to the laminate by interacting more strongly with the polar surface of the foil.

Comparative example L demonstrates the utility of the styrene-butadiene block copolymer in providing a smooth and uniform coating when both types of poly(arylene ether) and the maleinated polybutadiene are present. In example L, in which the Kraton 1118 was omitted, the coating was noted to be "grainy" or non-uniform on a macroscopic size scale. It is hypothesized that the styrene-butadiene copolymer acts to compatibilize, at least on a macroscopic scale, the poly (arylene ether) polymer and maleinated polybutadiene polymers.

TABLE 7

| Component | 11 | 12 | 13 | 14 | 15 | 16 | H | I | J | K | L | M | N | P | Q |
|---|---|---|---|---|---|---|---|---|---|---|---|---|---|---|---|
| PPE-MA solution | 100 | 100 | 100 | 100 | 100 | — | — | — | 100 | 100 | 100 | — | — | — | — |
| KRATON D-1118 | 7.5 | 7.5 | 7.5 | 12.0 | 3.75 | 7.5 | 7.5 | — | — | 7.5 | — | 7.5 | — | 7.5 | — |
| RICON 184MA6 | 3.5 | 7.5 | 10.0 | 7.5 | 7.5 | 7.5 | — | 7.5 | — | — | 7.5 | 7.5 | — | — | — |
| Blendex HPP820 | — | — | — | — | — | 100 | — | — | — | — | — | — | — | — | — |
| BN1015 | — | — | — | — | — | — | — | — | — | — | — | — | 7.5 | — | — |
| Coating Appearance | Good | Good | Good | Good | Good | Good | Tacky | Tacky | Good | Good | Grainy | Tacky | Tacky | Tacky | — |

TABLE 7-continued

| Component | 11 | 12 | 13 | 14 | 15 | 16 | H | I | J | K | L | M | N | P | Q |
|---|---|---|---|---|---|---|---|---|---|---|---|---|---|---|---|
| Solder Float, 288° C. (pass/fail) | Pass | Pass | Pass | Pass | Pass | Pass | Pass | Pass | Fail | Fail | Pass | Pass | Pass | Pass | Pass |
| Copper Peel Strength (pli) | 4.70 | 4.75 | 4.67 | 4.26 | 4.60 | 4.60 | 3.2 | 2.85 | 5.2 | — | 4.88 | 3.45 | 2.70 | 2.75 | 3.0 |

P = Pass;
F = Fail

Examples 17-23

These Examples demonstrate the suitability of these adhesive formulations for effective and economical coating on standard production equipment, as well as the wide range of formulations over which the copper peel strength and high temperature resistance are improved.

Commercial scale coating trials of 25-inch (63.5-centimeter) wide rolls of copper foil were conducted on a slot die coater using the formulations shown in Table 8 (amounts shown are in grams). The six formulations we coated at line speeds of 30 feet/minute (fpm) (9.14 meter/minute) onto both Gould TWS high profile copper foil and Oak Mitsui MLS-TOC-500-LZ reverse-treated (low profile) copper foil (Ex. 17-Ex. 22). Formulation 20 was also coated at 60 fpm, simply to demonstrate that higher speed coating was possible (Ex. 23). The coating basis weights ranged from 6 to 8 gsm. The samples were dried in a three-zone in-line oven with drying temperatures of 100° C., 125° C., and 150° C. Approximately 250 linear feet (76.2 linear meters) of useable material was coated for each formulation and copper foil type.

Each sample of coated copper foil was laminated to six sheets of 0.003-inch (0.0076-centimeter) RO4350B prepreg to form a 0.020 inches (0.0508 centimeters) thick laminate using the above press cycle, and tested.

The data for room temperature peel strength, hot oil peel strength, and solder float testing are reported in Table 8.

TABLE 8

| Component | Ex. 17 | Ex. 18 | Ex. 19 | Ex. 20 | Ex. 21 | Ex. 22 | Ex. 23 |
|---|---|---|---|---|---|---|---|
| Toluene | 12540 | 12540 | 12000 | 12000 | 11500 | 12000 | 12000 |
| Xylene | 577 | 577 | 577 | 577 | 525 | 577 | 577 |
| Blendex | 1039 | — | 1039 | 1039 | — | — | 1039 |
| PPE (Asahi) | — | 1039 | — | — | 945 | 1039 | — |
| Kraton | 808 | 808 | 404 | 808 | 735 | 404 | 808 |
| Ricon 184 MA6 | 1617 | 1617 | 1617 | 2079 | 1890 | 1617 | 2079 |
| Varox + Toluene | 52 + 100 | 52 + 100 | 50 + 100 | 52 + 100 | 52 + 100 | 50 + 100 | 52 + 100 |
| Results with MLS-TOC-500-LZ Copper Foil | | | | | | | |
| Copper Peel (pli) | 6.3 | 6.0 | 7.2 | 5.9 | 4.9 | 5.1 | 5.2 |
| Hot Oil Peel, 150° C. (pli) | 3.2 | 3.2 | 3.4 | 3.4 | — | — | 3.2 |
| Hot Oil Peel, 200° C. (pli) | 2.1 | 2.0 | 2.2 | 2.0 | — | — | 2.0 |
| Solder Float, 288° C., 10 sec. × 5 (pass/fail) | Pass | Pass | Pass | Pass | Pass | — | Pass |
| Coating Weight, gsm | 7.8 | 7.4 | 8.4 | 8.1 | — | — | 6.0 |
| DK at 10 GHz | 3.53 | 3.53 | 3.53 | 3.53 | — | — | 3.51 |
| DF at 10 GHz | 0.0042 | 0.0044 | 0.0043 | 0.0044 | — | — | 0.0041 |
| Z-CTE (ppm/° C.) | 45 | — | — | — | — | — | 43 |
| Results with TWS Copper Foil | | | | | | | |
| Copper Peel (pli) | 6.8 | 7.1 | 6.9 | 5.9 | 6.1 | 6.1 | 6.2 |
| Hot Oil Peel, 150° C. (pli) | 3.8 | 3.8 | 3.9 | 3.6 | — | — | 3.6 |
| Hot Oil Peel, 200° C. (pli) | 2.8 | 2.7 | 3.1 | 2.5 | — | — | 2.4 |
| Solder Float, 288° C., 10 sec. × 5 (pass/fail) | Pass | Pass | Pass | Pass | Pass | — | Pass |
| Coating Weight (gsm) | 7.5 | 7.7 | 8.1 | 7.8 | 7.4 | — | 6.3 |
| DK at 10 GHz | 3.50 | 3.49 | 3.48 | 3.47 | — | — | 3.51 |
| DF at 10 GHz | 0.0045 | 0.0044 | 0.0043 | 0.0043 | — | — | 0.0042 |

Peel strength values for the uncoated TWS copper are about 3.5 pli and the value for the uncoated MLS-TOC-500 copper is less than 2 pli (data not shown). The hot oil peel strength data above demonstrate sufficient bond at high temperature to allow for robust "reworkability." The CTE, dielectric constant and loss tangent data show that the adhesive coating does not have a deleterious effect on these properties.

The examples in Tables 9-14 demonstrate the usefulness of the addition of nitrogen-containing compounds to magnesium-hydroxide-containing compositions. In general, these compositions were processed as follows for Examples 24-51. First, the resins, magnesium hydroxide, and all other components were thoroughly mixed to form a slurry in conventional mixing equipment. The mixing temperature was regulated to avoid substantial decomposition of the curing agent (and thus premature cure). Next, conventional prepreg manufacturing methods were employed. Typically, if used, the web was impregnated with the slurry, metered to the correct thickness, and then solvent was removed (evaporated to form a prepreg). The lamination process entailed a stack-up of 6 prepreg layers between two sheets of copper foils (Oak Mitsui TOC 500 LZ or Circuit Foil TWS) uncoated or previously coated with the adhesive layer. This stack-up was then densified and cured via flat bed lamination; typical cure temperature ranges were between about 325° F. (163° C.) and about 475° F. (246° C.) and pressure between 300-1200 psi.

In Examples 24-51, flame retardance was measured in accordance with UL-94. The designation "fail" indicates that the sample did not attain V-1. Dielectric constant (DK) and Dissipation Factor (DF) are the averages of the measured dielectric constants and dissipation factors from 1-10 Ghz frequency sweep. As previously noted, copper peel strength was measured in accordance with the "Peel strength of metallic clad laminates" test method (IPC-TM-650 2.4.8). Water absorption was measured in accordance with the test method, IPC-TM-650 2.6.2.1 (conditioned in an environment maintained at 50% relative humidity and 22° C. for 1 hour (prior to soaking in water).

In the xylene absorption test, 2" square laminate samples (2 pcs) were dried at 105 C for 1 hour and conditioned in an environment maintained at 50% relative humidity and 22° C. for 1 hour. The weight of each conditioned sample was determined to the nearest 0.1 milligram. The conditioned samples were then submersed in xylene at 22° C. for 24 hours. At the end of 24 hours, the laminate samples were removed from xylene one at time, all surface xylene was removed with a dry cloth, and the samples weighed immediately thereafter. Percent xylene absorption was calculated as follows:

$$\text{Xylene absorption (\%)} = \frac{\text{Wet weight} - \text{conditioned weight}}{\text{Conditioned weight}} \times 100$$

In the acid weight loss test, 2" square laminate samples (2 pieces) were dried at 105° C. for 1 hour and conditioned in an environment maintained at 50% relative humidity and 72° F. for 1 hour. The weight of each conditioned sample was determined to the nearest 0.1 milligram. The conditioned samples were then submersed in 10% by weight sulfuric acid at 70° C. for 20 minutes. At the end of 20 minutes, the laminate samples were removed from acid, washed thoroughly with water, dried, and conditioned. The weight of each conditioned sample was determined to the nearest 0.1 milligram. Percent acid loss was calculated as follows:

$$\text{Acid weight loss (\%)} = \frac{\text{Conditioned weight} - \text{Final weight}}{\text{Conditioned weight}} \times 100$$

The composition and test results of each prepared example are shown in Tables 9-14.

TABLE 9

| Component | Ex. 24 | Ex. 25 | Ex. 26 | Ex. 27 |
|---|---|---|---|---|
| Kraton D-1118 | 24.2 | 24.2 | 24.2 | 24.2 |
| A74NT | 2.0 | 2.0 | 2.0 | 2.0 |
| Trilene 65 | 10.1 | 10.1 | 10.1 | 10.1 |
| B-3000 | 79.0 | 79.0 | 79.0 | 79.0 |
| MGZ-6R (flame ret.) | 400 | 400 | 250 | 250 |
| Naugard XL | 0.5 | 0.5 | 0.5 | 0.5 |
| Perkadox 30 | 2.2 | 2.2 | — | — |
| TRIC | — | 10.0 | — | — |
| Varox | — | — | 2.2 | 2.2 |
| MC-15 | — | — | 50 | — |
| Melapur 2000 | — | — | — | 50 |
| Properties | | | | |
| DK at 10 GHz | 4.12 | 4.10 | 4.06 | 4.13 |
| DF at 10 GHz | 0.0046 | 0.0047 | 0.0053 | 0.0056 |
| Solder Float, 288° C., 10 sec. × 5 (pass/fail) | Pass | Pass | Pass | Pass |
| Flammability UL-94 | V0 | V0 | V0 | V0 |

Examples 24-27 in Table 9 demonstrate the effect of the magnesium hydroxide flame retardant on the flammability and the electrical properties of the circuit materials. Examples 26 and 27 demonstrate the effect of adding different nitrogen compounds and reducing the amount of magnesium hydroxide flame retardant on the flammability and electrical properties of the same circuit subassemblies. The magnesium hydroxide produced a halogen-free RO4350B thermoset substrate composition having a UL-94 rating of V0 in Examples 24 and 25 from Table 9. Examples 26 and 27 demonstrate that the addition of nitrogen-containing compounds permit the reduction of magnesium hydroxide content without sacrificing either the electrical properties or the flammability rating of the halogen free RO4350B composition.

Examples 28-37 in Tables 10 and 11 further examine the effect of different nitrogen compounds on the properties of magnesium hydroxide flame retardant containing circuit subassembly compositions. Particularly, some the nitrogen-containing compounds in the examples can reduce the concentration of magnesium hydroxide required in the composition while maintaining flame retardant properties.

The example 24 formulation, without the nitrogen-containing compound, had a weight ratio of RO4350B resin (Kraton, Trilene, and B3000) to magnesium hydroxide (MGZ-6R) of 1:3.57. This original formulation had a specific gravity for 20 mil laminates of 1.67 and a xylene absorption of greater than 7.0 percent. The calculated specific gravity and xylene absorption of standard RO4350B resin without magnesium hydroxide is 1.84 and about 1.5%, respectively. In testing, the original formulation using the magnesium hydroxide suffered about a 70% bond loss in the Electroless Nickel Immersion Gold (ENIG) process due to porosity in the laminate, most likely caused by the high concentration of MGZ-6R.

Table 10 illustrates the use of two types of nitrogen-containing compounds (melamine cyanurate MC-15, and melamine polyphosphate Melapur 200) in reducing magnesium hydroxide content in the subassemblies. The formulation used in each example contained 25-30 weight percent less MGZ-6R than in the original formulation.

TABLE 10

| Component | Ex. 28 | Ex. 29 | Ex. 30 | Ex. 31 | Ex. 32 | Ex. 33 |
|---|---|---|---|---|---|---|
| Kraton D-1118 | 24.4 | 24.4 | 24.4 | 24.4 | 24.4 | 24.4 |
| Trilene 65 | 10.1 | 10.1 | 10.1 | 10.1 | 10.1 | 10.1 |
| B3000 | 79.0 | 79.0 | 79.0 | 79.0 | 79.0 | 79.0 |
| MC-15 | 50.0 | 50.0 | 50.0 | 25.0 | 25.0 | 25.0 |
| MGZ-6R | 300.0 | 275.0 | 250.0 | 300.0 | 275.0 | 250.0 |
| Test Results | | | | | | |
| Laminate Thickness (mils) | 24 | 21 | 23 | 21.5 | 20 | 22 |
| Flammability (UL-94) | V0 | V0 | V0 | ~V0 | ~V0 | V1 |
| Bond, pli | 3.89 | 3.85 | 3.93 | 4.37 | 4.35 | 4.64 |
| Solder Float, 288° C., 10 sec. × 5 (pass/fail) | Pass | Pass | Pass | Pass | Pass | Pass |
| Specific Gravity | 1.77 | 1.80 | 1.77 | 1.79 | 1.80 | 1.77 |
| Xylene Absorption (%) | 1.67 | 1.08 | 1.05 | 1.17 | 1.00 | 1.09 |
| DK at 10 GHz | 4.08 | 4.10 | 4.06 | 4.12 | 4.07 | 4.05 |
| DF at 10 GHz | 0.005 | 0.005 | 0.0053 | 0.0054 | 0.0051 | 0.0047 |
| Z-axis CTE (ppm/° C.) | — | 56.51 | 57.48 | — | — | — |
| Water Absorption (%) | 0.19 | 0.16 | 0.13 | 0.17 | 0.16 | 0.12 |

The melamine cyanurate (MC-15) or the melamine polyphosphate (Melapur 200) addition to the resin composition increased the specific gravity to a range of 1.77 to 1.81 for all examples in Tables 10 and 11. The 25-30% reduction in magnesium hydroxide made possible by the addition of the nitrogen-containing compound to maintain flammability levels, allowed the resin composition to return to about the desirable specific gravity levels for the resin composition without the flame retardant. The same effect is seen with the xylene absorption, where the absorption percentages in all samples (1.00-1.67%) were decreased by the addition of nitrogen-containing compound and reduction of magnesium hydroxide. Again, the xylene absorption values more closely reflect those seen in resin compositions not having halogen free flame retardants. By adding the nitrogen-containing compound, therefore, the magnesium hydroxide concentration in the resin composition can advantageously be reduced. As a result, the addition of the nitrogen-containing compound can help to eliminate the porosity and other bonding issues found to be associated with high magnesium hydroxide flame retardant content.

TABLE 11

| Component | Ex. 34 | Ex. 35 | Ex. 36 | Ex. 37 |
|---|---|---|---|---|
| Kraton D-1118 | 24.4 | 24.4 | 24.4 | 24.4 |
| Trilene 65 | 10.1 | 10.1 | 10.1 | 10.1 |
| B3000 | 79.0 | 79.0 | 79.0 | 79.0 |
| MC-15 | 50.0 | 50.0 | 25.0 | — |
| Melapur 200 | — | — | — | 50.0 |
| MGZ-6R-2 | 275.0 | 250.0 | 300.0 | 250.0 |
| Test Results | | | | |
| Laminate Thickness (mils) | 20.5 | 20.5 | 23.0 | 21.0 |
| Flammability (UL-94) | V0 | V0 | V1 | V0 |
| Bond, pli | 3.82 | 3.93 | 4.25 | 3.85 |
| Solder Float, 288° C., 10 sec. × 5 (pass/fail) | Pass | Pass | Pass | Pass |
| Specific Gravity | 1.81 | 1.77 | 1.77 | 1.79 |
| Xylene Absorption (%) | 1.20 | 1.10 | 1.12 | 1.20 |
| DK at 10 GHz | 4.15 | 4.10 | 4.08 | 4.13 |
| DF at 10 GHz | 0.009 | 0.01 | 0.008 | 0.006 |

Examples 34-37 in Table 11 contained a higher grade of magnesium hydroxide (MGZ-6R-2), wherein the flame retardant had a higher bulk density. 0.60 gm/cubic centimeter. While the dissipation factors with the examples using this grade were higher, the examples did not show significant improvement in specific gravity or xylene absorption over the lower bulk density grade of magnesium hydroxide (MGZ-6R). There does seem to be an indication, however, that the two different nitrogen-containing additives create the possibility of a laminate having an intermediate flammability rating (i.e., V1). Examples 33 and 36, each containing 25 grams of MC-15, had UL-94 ratings of V1.

To reiterate, the examples 28-37 examine the effect of different nitrogen compounds on the properties of magnesium hydroxide flame retardant containing circuit subassembly compositions. Particularly, some of the nitrogen-containing compounds in the examples can reduce the concentration of magnesium hydroxide required in the composition while maintaining flame retardant properties and preventing porosity and bond loss issues for the laminate.

The examples in Tables 12-14 demonstrate the benefits of the special adhesive layer between the dielectric and the copper foil, when used in combination with the novel magnesium hydroxide/nitrogen-containing compound mixtures.

Specifically, examples 38-41 in Table 12 demonstrate the effect of the magnesium hydroxide, nitrogen-containing compound combination, and the adhesion layer on flammability, acid weight loss and bond. In particular, examples 38, 39, and 41 demonstrate that the adhesive layer reduces acid weight loss. Also, example 41, compared with examples 39 and 40, shows that the magnesium hydroxide/nitrogen-containing compound mixture in combination with the adhesive layer can achieve high flame retardancy with a reduced amount of magnesium hydroxide, while maintaining good electrical properties and low water and xylene absorption.

TABLE 12

| | Ex. 38 | Ex. 39 | Ex. 40 | Ex. 41 |
|---|---|---|---|---|
| RO4350B Resins | 113.3 | 113.3 | 113.3 | 113.3 |
| A174NT | 2.0 | 2.0 | 2.0 | 2.0 |
| MGZ-6R | 400 | 400 | 300 | 300 |

TABLE 12-continued

|  | Ex. 38 | Ex. 39 | Ex. 40 | Ex. 41 |
|---|---|---|---|---|
| Melapur 200 | — | — | — | 50 |
| Antioxidant | 0.6 | 0.6 | 0.6 | 0.6 |
| Varox-Curing Agent | 2.2 | 2.2 | 2.2 | 2.2 |
| Coated LZ Copper (0.5 oz) | No | Yes | No | Yes |
| Bond, pli | 0.52 | 5.30 | 2.60 | 6.22 |
| Flammability (UL-94) | V0 | V0 | Fail | V0 |
| Acid Weight Loss, % | 0.96 | 0.35 | 0.82 | 0.55 |
| Water Abs., %, 24 h | 0.76 | 0.45 | 0.18 | 0.28 |
| Xylene Abs. %, 24 h | 7.54 | 4.04 | 1.12 | 1.52 |

Examples 42-45 in Table 13 examine the effect of different nitrogen compounds on the properties of magnesium hydroxide containing circuit subassembly compositions. The results shows that the different nitrogen compounds all give the desired V-0 flame retardance, while maintaining other desired performance properties, when the laminates include the special adhesive layer. When compared to examples 38 and 39, examples 42-45 clearly show that use of three different nitrogen compounds reduces the magnesium hydroxide content in the dielectrics. Specifically, the formulations in examples 42-45 used about 25% less magnesium hydroxide than the formulations in 38 and 39.

TABLE 13

|  | Ex. 42 | Ex. 43 | Ex. 44 | Ex. 45 |
|---|---|---|---|---|
| RO4350B Resins | 113.3 | 113.3 | 113.3 | 113.3 |
| A174NT | 2.0 | 2.0 | 2.0 | 2.0 |
| MGZ-6R | 300 | 300 | 300 | — |
| MC-15 | — | — | 35 | — |
| Melem 350 | — | — | — | 35 |
| Budit 3141CA* | 35 | 35 | — | — |
| Antioxidant | 0.6 | 0.6 | 0.6 | 0.6 |
| Varox-Curing Agent | 2.5 | — | 2.2 | — |
| TAIC | — | 18 | — | 18 |
| Perkadox | — | 3.5 | — | 3.5 |
| Coated LZ Copper (0.5 oz) | Yes | Yes | Yes | No |
| Bond, pli | 6.63 | 5.92 | 5.50 | — |
| Test results |  |  |  |  |
| Flammability (UL-94) | V0 | V0 | V-0 | V-1 |
| Acid Wt. Loss* % | 0.42 | 0.31 | 0.25 | — |
| Water Abs., %, 24 h | 0.3 | 0.25 | 0.24 | — |
| Xylene Abs. %, 24 h | 1.49 | 1.38 | 1.67 | — |

TABLE 13-continued

|  | Ex. 42 | Ex. 43 | Ex. 44 | Ex. 45 |
|---|---|---|---|---|
| DK (at 10 GHz) | 4.20 | 4.22 | 4.10 | — |
| DF (at 10 GHz) | 0.0048 | 0.0051 | 0.0053 | — |

*Melem 350 from Delamin Ltd in UK

Examples 47-51 in Table 14 examine the effect of two other magnesium hydroxides, which likely differ from the MGZ-6R of previous examples in the coating technology used in their manufacture. While there are some minor differences in the resulting laminates' properties, these different magnesium hydroxides continue to show the benefits of the combination of magnesium hydroxide and a nitrogen-containing compound with use of the special adhesive layer in achieving V-1 or better flame retardance with good adhesive bond strength and low acid weight loss.

TABLE 14

|  | Ex. 46 | Ex. 47 | Ex. 48 | Ex. 49 | Ex. 50 | Ex. 51 |
|---|---|---|---|---|---|---|
| RO4350B Resins 113.3 | 113.3 | 113.3 | 113.3 | 113.3 | 113.3 | 113.3 |
| A174NT | 1.0 | 1.0 | 1.0 | 2.0 | 2.0 | 2.5 |
| Kisuma 8SN | 286 | 300 | 270 | — | 360 | 190 |
| Magseeds EP1-A7 | — | — | — | 300 | — | — |
| CE44IR | 90 | 100 | 20 | — | 100 | 120 |
| Fluon (G580) | — | — | — | — | 60 | — |
| Budit 3141CA | — | 34 | 50 | 40 | — | 30 |
| Antioxidant | 1.2 | 1.2 | 1.2 | 1.2 | 0.6 | 0.6 |
| Varox-Curing Agent | 2.2 | — | 2.4 | 2.2 | 2.2 | — |
| TAIC | — | 18 | — | — | — | 18 |
| Perkadox | — | 3.5 | — | — | — | 3.5 |
| Coated LZ Copper (0.5 oz) | Yes | Yes | Yes | Yes | Yes | Yes |
| Bond, pli | — | 5.10 | 5.61 | 6.07 | 5.4 | — |
| Flammability (UL-94) | Fail | V0 | V-0 | V-1 | V-1 | V-1 |
| Acid Weight Loss*, % | 0.8 | 0.60 | 0.79 | 0.81 | 0.5 | 1.17 |
| Water Abs., %, 24 h | — | 0.31 | 0.33 | — | 0.11 | — |
| Xylene Abs. %, 24 h | 3.04 | 1.21 | 1.80 | 1.23 | 1.40 | — |
| DK (at 10 GHz) | — | 4.29 | 4.20 | 4.48 | 4.02 | — |
| DF (at 10 GHz) | — | 0.003 | 0.005 | 0.0043 | 0.0032 | — |

*Acid wt. loss % without coated copper (no adhesive layer) for examples 9 to 13 were 8-12%.

The examples of Table 15 demonstrate certain benefits of alternative adhesive compositions, in particular the use of a second polybutadiene, which is a syndiotactic polybutadiene homopolymer, JSR 810, in replacement of the elastomeric block copolymer, Kraton 1118. In the table the examples 52 A, B and C differ from examples 53 A, B and C in substrate composition. Major differences are in filler type and content, with the 53 compositions having significantly lower filler content.

Additionally, in Table 15, the "B" examples differ from the "A" examples in the use of JSR 810, syndiotactic polybutadiene, instead of Kraton 1118K, elastomer block copolymer in the adhesive. The "C" examples differ from the "B" examples in the use of fused silica filler in the adhesive.

Comparing examples 52 C and 52 B to 52 A, all with the same substrate composition, the changes in adhesion composition do not have a significant impact on solder resistance and copper bond of resulting laminates: but with the alternate substrate composition of examples 53, the changes in adhesive composition markedly improve solder resistance and increase copper bond (compare 53 B and 53 C to 53 A). Also, the laminate results show that addition of filler to the adhesive significantly lowers Z axis CTE.

Another benefit of the combination of the 53 substrate composition with the JSR 810 modification of the adhesive is a reduction in the dielectric constant of the resulting laminate, as seen by comparing the DK result of 53 B to 52 A.

Finally, it should be noted that the examples in Table 15 all have a UL94 flammability rating of V0.

TABLE 15

| Circuit Substrate Composition | Ex. 52A | Ex. 52B | Ex. 52C | Ex. 53A | Ex. 53B | Ex. 53C |
|---|---|---|---|---|---|---|
| RO4350B Resins | 63.80 | 63.80 | 63.80 | 47.90 | 47.90 | 47.90 |
| Ricon 257 | — | — | — | 13.0 | 1.0 | 1.0 |
| A174NT | 1.72 | 1.72 | 1.72 | 0.5 | 0.5 | 0.5 |
| Teccosphere CE44I | 124.0 | 124.0 | 124.0 | — | — | — |
| Teccosphere CE44IR | 61.29 | 61.29 | 61.29 | — | — | — |
| BA 188 | — | — | — | 40.0 | 40.0 | 40.0 |
| BT93 WFG | 28.28 | 28.28 | 28.28 | 35.0 | 35.0 | 35.0 |
| Antioxidant | 0.60 | 0.60 | 0.60 | 0.40 | 0.40 | 0.40 |
| Peroxide Curing Agent | 1.28 | 1.28 | 1.20 | 1.20 | 1.20 | 1.20 |
| Adhesive Composition | | | | | | |
| Blendex HPP820 | 10.0 | 10.0 | 10.0 | 10.0 | 10.0 | 10.0 |
| Kraton 1118 | 7.5 | — | — | 7.5 | — | — |
| JSR 810 | — | 7.5 | 7.5 | — | 7.5 | 7.5 |
| Ricon 184MA6 | 7.5 | 7.5 | 7.5 | 7.5 | 7.5 | 7.5 |
| BA 188 | — | — | 16.0 | — | — | 16.0 |
| Laminate Test Results | | | | | | |
| Laminate Thickness (2 plies), mil | 7.1 | 7.1 | 7.3 | 5.50 | 5.50 | 5.70 |
| Solder Float 288° C. (5 × 10 sec) | Pass | Pass | Pass | Fail | Pass | Pass |
| Bond (0.5 oz MLS), pli | 5.20 | 5.0 | 5.1 | 2.40 | 4.1 | 4.30 |
| Z-CTE (0-250° C.), ppm | — | — | — | 102 | 108 | 49.20 |
| DK/DF @ 10 GHz | 3.5/0.004 | — | — | — | 3.25/0.004 | — |

The singular forms "a," "an," and "the" include plural referents unless the context clearly dictates otherwise. The endpoints of all ranges directed to the same characteristic or component are independently combinable and inclusive of the recited endpoint. All references are incorporated herein by reference. As used herein and throughout, "disposed," "contacted," and variants thereof refers to the complete or partial physical contact between the respective materials, substrates, layers, films, and the like. Further, the terms "first," "second," and the like herein do not denote any order, quantity, or importance, but rather are used to distinguish one element from another.

While specific embodiments have been shown and described, various modifications and substitutions can be made thereto without departing from the spirit and scope of the invention. Accordingly, it is to be understood that the present invention has been described by way of illustration and not limitation.

What is claimed is:

1. A circuit subassembly, comprising
a conductive layer;
a dielectric layer formed from a thermosetting composition, wherein the thermosetting composition comprises, based on the total weight of the thermosetting composition:
a polybutadiene or polyisoprene resin,
about 30 to about 70 percent by weight of a magnesium hydroxide having less than about 1000 ppm of ionic contaminants, and
about 5 to about 15 percent by weight of a nitrogen-containing compound, wherein the nitrogen-containing compound comprises at least about 15 weight percent of nitrogen; and
an adhesive layer disposed between and in contact with the conductive layer and the dielectric layer, wherein the adhesive comprises a poly(arylene ether) and a polybutadiene polymer, a polyisoprene polymer, or a combination thereof;
wherein the circuit subassembly has a UL-94 rating of at least V-1; and
wherein the circuit subassembly has a combined bromine and chlorine content of less than about 900 ppm; a water absorption of less than 0.5 percent after submersion in water at 23° C. for 24 hours; a xylene absorption of less than 2% by weight, after a test sample having dimensions of 2 inches ×2 inches ×20 mils is submerged in xylene at 23° C. for 24 hours; and an acid weight loss less of not more than 0.81% after submersion in 10 wt.% sulfuric acid at 70° C. for 20 minutes.

2. The circuit subassembly of claim 1, wherein the nitrogen-containing compound is a melamine polyphosphate, a melamine cyanurate, or a combination comprising at least one of the foregoing compounds.

3. The circuit subassembly of claim 1, wherein the poly(arylene ether) is carboxy-functionalized.

4. The circuit subassembly of claim 3, wherein the poly(arylene ether) is the reaction product of a poly(arylene ether) and maleic anhydride.

5. The circuit subassembly of claim 1, wherein the adhesive layer further comprises a polybutadiene polymer, a polyisoprene polymer, or a combination comprising at least one of the foregoing polymers.

6. The circuit subassembly of claim 5, wherein the polybutadiene polymer or polyisoprene polymer in the adhesive layer is carboxy-functionalized.

7. The circuit subassembly of claim 6, wherein the polybutadiene polymer or polyisoprene polymer in the adhesive layer is a maleinized polybutadiene-styrene copolymer or a maleinized polyisoprene-styrene copolymer.

8. The circuit subassembly of claim 1, wherein the adhesive layer comprises a syndiotactic polybutadiene polymer, optionally together with a different a polybutadiene polymer, a polyisoprene polymer, or a combination comprising at least one of the foregoing polymers.

9. The circuit subassembly of claim 1, wherein the adhesive layer further comprises an elastomeric polymer.

10. The circuit subassembly of claim 9, wherein the elastomeric polymer is a block copolymer comprising units derived from an alkenyl aromatic compound and a conjugated diene.

11. The circuit subassembly of claim 1, wherein the adhesive layer further comprises a filler.

12. The circuit subassembly of claim 1, wherein the circuit material has a UL-94 rating of at least V-0.

13. A circuit subassembly, comprising:
a conductive layer;
a dielectric layer formed from a thermosetting composition, wherein the thermosetting composition comprises, based on the total weight of the thermosetting composition
a polybutadiene or polyisoprene resin, and
about 50 to about 80 percent by weight, of a magnesium hydroxide having less than about 1000 ppm of an ionic contaminant; and
an adhesive layer disposed between and in intimate contact with the conductive layer and the dielectric layer, wherein the adhesive layer comprises a poly(arylene ether) and a polybutadiene polymer, a polyisoprene polymer, or a combination thereof;
wherein the circuit material has a UL-94 rating of at least V-1; and
wherein the circuit subassembly has a combined bromine and chlorine content of less than about 900 ppm; a water absorption of less than 0.5 percent after submersion in water at 23° C. for 24 hours; a xylene absorption of less than 2% by weight, after a test sample having dimensions of 2 inches ×2 inches ×20 mils is submerged in xylene at 23° C. for 24 hours; and an acid weight loss less of not more than 0.81% after submersion in 10 wt.% sulfuric acid at 70° C. for 20 minutes.

14. The circuit subassembly of claim 13, wherein the poly(arylene ether) is carboxy-functionalized.

15. The circuit subassembly of claim 14, wherein the poly(arylene ether) is the reaction product of a poly(arylene ether) and maleic anhydride.

16. The circuit subassembly of claim 13, wherein the polybutadiene polymer or polyisoprene polymer in the adhesive layer is carboxy-functionalized.

17. The circuit subassembly of claim 13, wherein the adhesive layer comprises a syndiotactic polybutadiene polymer, optionally together with a different a polybutadiene polymer, a polyisoprene polymer, or a combination comprising at least one of the foregoing polymers.

18. The circuit subassembly of claim 13, wherein the adhesive layer further comprises an elastomeric polymer.

19. The circuit subassembly of claim 18, wherein the elastomeric polymer is a block copolymer comprising units derived from an alkenyl aromatic compound and a conjugated diene.

20. The circuit subassembly of claim 13, wherein the adhesive layer further comprises a filler.

21. The circuit subassembly of claim 13, wherein the conductive layer is patterned to form a circuit.

22. The circuit subassembly of claim 13, wherein the circuit material has a UL-94 rating of at least V-0.

* * * * *